(12) United States Patent
Tavabi et al.

(10) Patent No.: US 10,827,942 B2
(45) Date of Patent: Nov. 10, 2020

(54) DETECTING FATIGUE BASED ON ELECTROENCEPHALOGRAM (EEG) DATA

(71) Applicant: Intel Corporation, Santa Clara, CA (US)

(72) Inventors: Nazgol Tavabi, Encino, CA (US); Leili Tavabi, Encino, CA (US); Marissa Powers, Portland, OR (US); Esther Jun Kim, San Jose, CA (US); Olufemi B. Oluwafemi, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 281 days.

(21) Appl. No.: 15/860,866

(22) Filed: Jan. 3, 2018

(65) Prior Publication Data

US 2019/0038166 A1    Feb. 7, 2019

(51) Int. Cl.
| | | |
|---|---|---|
| *A61B 5/0478* | (2006.01) | |
| *A61B 5/18* | (2006.01) | |
| *G06F 3/01* | (2006.01) | |
| *A61B 5/16* | (2006.01) | |
| *A61B 5/048* | (2006.01) | |
| *A61B 5/00* | (2006.01) | |

(52) U.S. Cl.
CPC ............ *A61B 5/0478* (2013.01); *A61B 5/168* (2013.01); *A61B 5/18* (2013.01); *G06F 3/015* (2013.01); *A61B 5/048* (2013.01); *A61B 5/6814* (2013.01)

(58) Field of Classification Search
CPC ......... A61B 5/0478; A61B 5/18; A61B 5/168; A61B 5/048; A61B 5/6814; A61B 5/0476; A61B 5/0482; A61B 5/0484; A61B 5/165; G06F 3/015; G06F 3/012
See application file for complete search history.

(56) References Cited

U.S. PATENT DOCUMENTS

| | | | | |
|---|---|---|---|---|
| 6,070,098 | A * | 5/2000 | Moore-Ede | .......... A61B 5/1103 600/300 |
| 2011/0288424 | A1* | 11/2011 | Kanai | ...................... A61B 5/18 600/500 |

(Continued)

OTHER PUBLICATIONS

"Dry EEG Electrodes," Lopez-Gordo et al, Sensors, 2014 14, 12847-12870 (24 pages).

(Continued)

*Primary Examiner* — Matthew Kremer
*Assistant Examiner* — Avery M Foley
(74) *Attorney, Agent, or Firm* — Patent Capital Group

(57) ABSTRACT

In one aspect, an apparatus for detecting fatigue comprises a dry-contact electroencephalogram (EEG) electrode to measure EEG data operably coupled to at least one processor. The at least one processor is to: calculate a frequency domain representation of the EEG data, detect spectral features indicative of fatigue based on the frequency domain representation; and determine whether the brain is fatigued based on the detection. In another aspect, a method for detecting fatigue comprises receiving EEG data from dry-contact EEG electrode, calculating a frequency domain representation of the EEG data, detecting spectral features indicative of fatigue based on the frequency domain representation; and determining whether the brain is fatigued based on the detection.

24 Claims, 16 Drawing Sheets

(56) References Cited

U.S. PATENT DOCUMENTS

| | | | | |
|---|---|---|---|---|
| 2014/0316230 | A1* | 10/2014 | Denison | A61B 5/04012 600/383 |
| 2016/0320840 | A1* | 11/2016 | Hwang | G06F 3/015 |
| 2017/0065199 | A1* | 3/2017 | Meisel | A61B 5/0476 |
| 2018/0014741 | A1* | 1/2018 | Chou | G09B 19/003 |
| 2018/0133431 | A1* | 5/2018 | Malchano | A61N 1/36025 |
| 2019/0076643 | A1* | 3/2019 | Siegle | A61N 1/00 |

OTHER PUBLICATIONS

"EEG-based mental fatigue measurement using multi-class support vector machines with confidence estimate", Dhen KQ et al,, Clin. Neurophysiol. 2008; 119(7): 1524-1533, 1 page (Objective only).

"Guideline 5: Guidelines for Standard Electrode Position Nomenclature", American Clinical Neurophysiology Society, Copyright 2006 American Clinical Neurophysiology Society, 4 pages.

"IFCN standards for digital recording of clinical EEG," Nuwer et al , Electroencephalography and clinical Neurophysiology 106 (1998) 259-261, Elsevier Science Ireland Ltd, 1998 (3 pages).

"Psychophysiological investigation of vigilance decrement: Boredom or cognitive fatigue?", Pattyn et al., Physiology & Behavior 93 (2008) 369-378 (10 pages).

"Real-Time Nonintrusive Monitoring and Prediction of Driver Fatigue", Ji et al, IEEE Transactions on Vehicular Technology, vol. 53, No. 4, Jul. 2004, pp. 1052-1068 (17 pages).

"Simultaneous EEG Recordings with Dry and Wet Electrodes in Motor-Imagery", Saab et al., Max Planck Institute for Intelligent Systems, Dept. Empirical Inference, Tubingen, Germany, Graduate School of Neural and Behavioural Sciences—International Max Planck Research School, Tubingen, Germany, pp. 1-4.

"Using EEG spectral components to assess algorithms for detecting fatigue", Jap et al., Expert Systems with Applications 36 (2009) 2352-2359 (9 pages).

"Vigilance, monitoring, and search", Parasuraman, Raja, Article, Jan. 1986, Abstract only, 1 page.

* cited by examiner

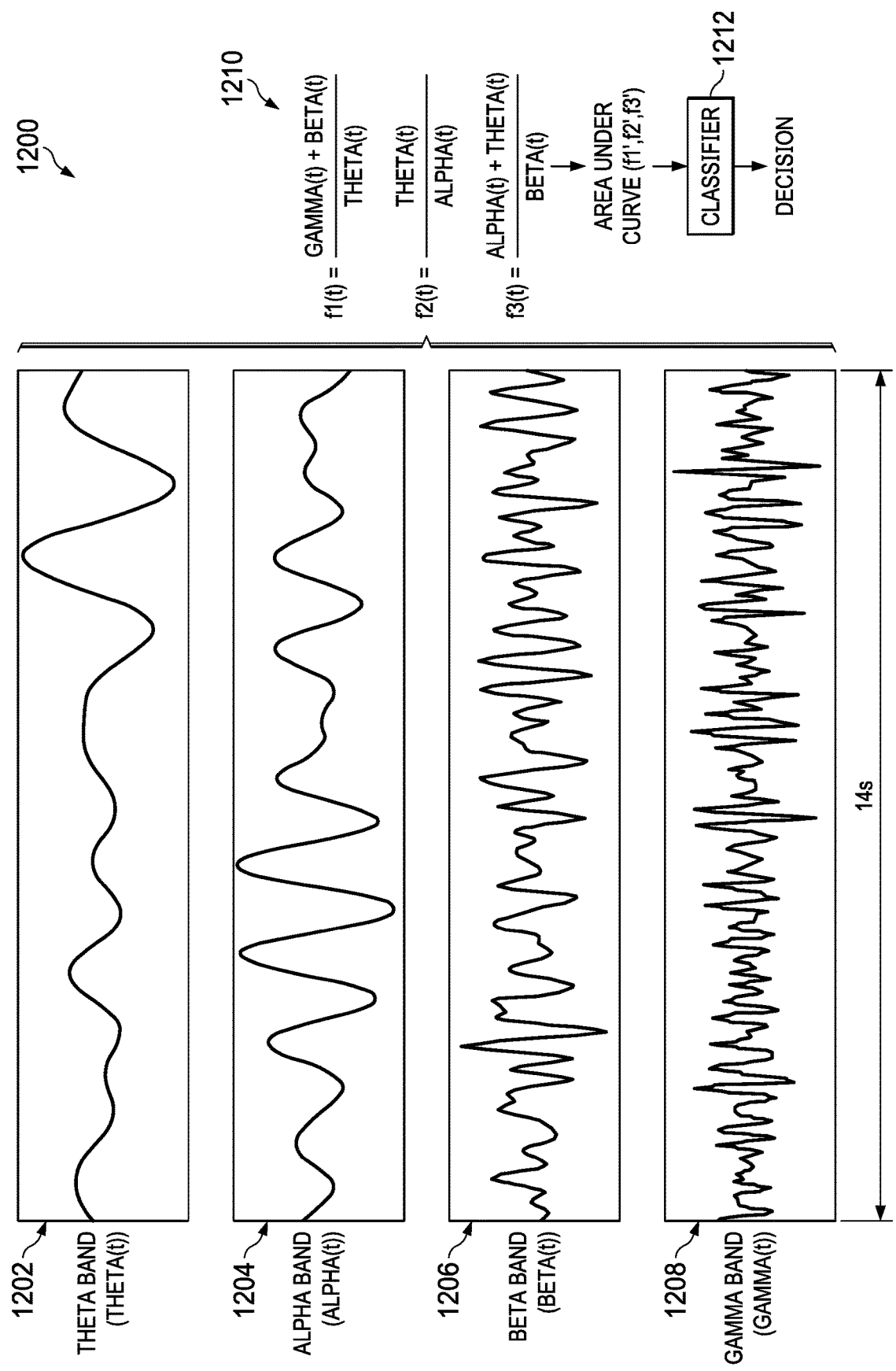

DETECTING FATIGUE BASED ON ELECTROENCEPHALOGRAM (EEG) DATA

TECHNICAL FIELD

Embodiments described generally relate to the field of fatigue detection and, in particular, to fatigue detection based on electroencephalogram (EEG) data.

BACKGROUND

A person can become fatigued (e.g., lose focus and, in some cases, fall asleep) while performing tasks over an extended period of time. For example, some monotonous tasks do not provide the person with enough stimulation to keep them engaged. A monotonous task, for example, may be a task that lasts for a long time but requires infrequent activity from a user. For example, the user may be required to maintain focus for an hour or more but active input may only be required about every 2-3 minutes. In some cases, a loss of focus could result in bodily harm to the person, bodily harm to another person, or equipment damage.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 12 illustrates a frequency domain representation of pre-frontal cortex EEG data from the truncated time window of FIG. 11B, according to some embodiments of the present disclosure.

DESCRIPTION OF EMBODIMENTS

Figure 1:
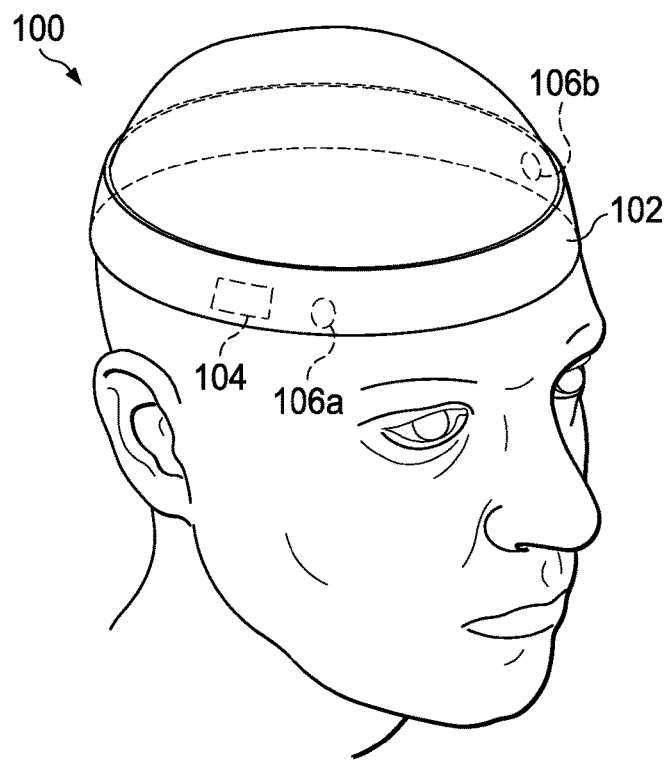
FIGS. 1, 2, and 3 illustrate head-mountable devices, according to some embodiments of the present disclosure.

A person can become fatigued (e.g., lose focus and, in some cases, fall asleep) while performing tasks over an extended period of time. For example, some monotonous tasks do not provide the person with enough stimulation to keep them engaged. A monotonous task, for example, may be a task that lasts for a long duration of time but only requires infrequent activity from a user. For example, the user may be required to maintain focus for an hour or more but active input may only be required about every 2-3 minutes. A user may progress from a loss of focus, to drowsiness (during which they may displays visible signs of drowsiness), and, finally, to falling asleep. For some tasks, a loss of focus could result in bodily harm to the person, another person, or result in equipment damage. Such tasks, may include, for example, operating a vehicle (e.g., a motor vehicle, a forklift) or operating machinery (e.g., a crane, a hydraulic or mechanical press). For other tasks, a loss of focus could result in the user not receiving information critical for a device (e.g., in a meeting, or a video game). There is a need for a system for fatigue detection that is applicable in a variety of environments.

A possible solution is to use images of a user to apply image processing techniques to detect fatigue (e.g., drowsiness) from visible indicators that appear in body movements and/or facial expressions (e.g., Percentage of Eye Closure (PERCLOS), facial expressions, and head drifts). These image-based techniques detect drowsiness too late to be effective for some applications. A user may progress from a loss of focus to drowsiness (during which they may displays visible signs of drowsiness) and, finally, they fall asleep. The image processing techniques detect drowsiness only after the driver displays visible signs of sleepiness, which is a much more advanced stage than loss of focus. A better solution would detect fatigue before the user is nearly asleep. Such image processing techniques are, therefore, incapable of predicting loss of focus since the preliminary indicators needed for image-based approaches only surface after the user is already in a fatigued state and, therefore, has already lost some focus.

Another possible solution is to use electroencephalogram (EEG) data measured from a user's brain to apply spectral processing techniques to detect fatigue (e.g., loss of focus). Electroencephalogram (EEG) electrodes are placed in contact with a user's skin (on the head) and record electrical activity of the user's brain. To understand technical challenges associated with an EEG-based approach to detecting fatigue, it is important to understand two basic classes of EEG electrodes: dry electrodes and wet electrodes. Wet electrodes utilize, e.g., electrophoresis gel between the electrode and the user's skin. The gel greatly improves the electrical conductivity between the skin and the electrode, which drastically improves the quality of the EEG data collected from the wet electrode. Wet electrodes can have an impedance of 20 kiloohms (kΩ) or less. Keeping the electrical resistance low (i.e., 20 kΩ or less) in wet electrodes helps to increase the quality of the EEG data produced therefrom. Consequently, the EEG data collected from a gel electrode is of a high-quality signal (e.g., with relatively little noise) due to the use of the gel. Dry electrodes (dry-contact) utilize no gel (and no other liquid) between the electrode and the user's skin. Thus, the electrodes are applied dry (expect, perhaps, for any bodily fluids produced by the user). There is potentially a gap between the electrode and the user's skin. In addition, dry electrodes can have an electrode impedance of 100 kΩ or more (and in some cases as high as 150 kΩ or 200 kΩ). The lack of a conduit (such a gel) reduces the electrical conductivity between the skin and the electrode and the relatively high impedance degrades the quality of the EEG data collected from the dry electrode. Consequently, the EEG data collected from a dry electrode is of a low-quality signal (e.g., with relatively high noise). Artifacts can be produced when the user blinks their eyes, frowns, other muscle movements nearby the electrode. Such artifacts can have $100x$ the magnitude of EEG data from the brain and therefore can overshadow the EEG signal when present. Dry electrodes are much more susceptible to such artifacts than wet electrodes. Such artifacts produce a more significant signal disturbance for dry electrodes than they do for wet electrodes.

Wet electrodes are impractical for users, especially when used in applications in which a user is mobile. Because wet electrodes require a user to put gel on their head (e.g., in their hair), they are inconvenient in some environments (e.g., in a work setting). Wet electrodes may be expensive and, therefore, cost prohibitive. Some system that use wet electrodes (e.g., medical-grade EEG systems) are cumbersome and immobile, rendering such systems not practically useful for mobile applications. Some dry electrodes puncture the skin, however, the needles that puncture the skin can easily break in many settings.

A technical challenge exists when viewed in the context of a combination of the choice of type of EEG electrode and processing required for EEG data measured from the EEG electrode. Because wet electrodes are impractical for some applications, dry electrodes are a better choice for such applications. However, because EEG data from dry electrodes, in general, contains more noise than EEG data from wet electrodes, the processing techniques used to analyze the EEG data from wet electrodes may not function as well on the relatively noisy EEG data from dry electrodes. In addition, EEG data from dry electrodes that only rest atop the skin (i.e., do not puncture the skin), in general, contains more noise than EEG data from dry electrodes that puncture the skin. There is a need for a system for fatigue detection that is robust with respect to noise and is mobile (e.g., can be discretely utilized in a work environment without gel, and without risk of needles breaking). There is a need for a system that can provide a robust detection of fatigue based on EEG data from dry electrodes.

A solution disclosed herein utilizes a unique combination of spectral features to provide robust fatigue detection when used with dry-contact EEG electrodes (which can produce a relatively noisy EEG signal). A classier uses EEG data to determine that a user is fatigued and/or to predict that a user will be fatigued within a predictive a window of time (e.g., a vigilance decrement state used as a proxy for loss of focus). The input to the classifier comprises features of several combinations of frequency bands extracted from EEG data. As a non-limiting example, a support vector machine (SVM) classifier using a sigmoid kernel may be trained to detect and/or predict fatigue based on EEG data. An output of the classifier includes data indicative of whether the user is fatigued (i.e., based on a state of vigilance decrement).

An article titled, "Psychophysiological investigation of vigilance decrement: Boredom or cognitive fatigue?" by N. Pattyn et al. (published in *Physiology & Behavior*, Volume 93, January 2008, pp. 369-378), describes vigilance decrement as a slowing in reaction times or an increase in error rates as an effect of time-on-task during tedious monitoring tasks. In the present disclosure, vigilance decrement is inclusive of a state of EEG data (i.e., the vigilance decrement state) that corresponds to a loss of focus of the user as indicated by the user's reaction times (or predicted reaction times) in response to a stimulus. For example, when the user's reaction time is (or is predicted to be based on EEG data) greater than or equal to the threshold, the user is determined to be in the vigilance decrement state (i.e., has lost focus). When the user's reaction time is (or is predicted to be based on EEG data) less than the threshold, the user is determined to not be in the vigilance decrement state (i.e., has not lost focus). It is noted that, in the present disclosure, "fatigue" and "loss of focus" are used interchangeably.

The features include unique combinations of frequency bands, e.g.:
(1) a first combination of the magnitude of each of a gamma frequency band, the beta frequency band, and the theta frequency band;
(2) a second combination of the magnitude of each of the theta frequency and the alpha frequency; and
(3) a third combination of the magnitude of each of the alpha frequency, the theta frequency, and the beta frequency.

Advantageously, these combinations facilitate classifications that are robust with respect to noise and, thereby, enables the use of dry electrodes, which are mobile (e.g., can be discretely utilized many environments). The classification is robust in the sense that it is capable of detecting fatigue, without failure, in the presence of relatively high noise in the EEG data from dry electrodes. The classifier (including the combinations) may be deployed in a head-mountable device.

Advantageously, a head-mountable device according to the present disclosure detects a measure of fatigue of a user by executing instructions for a fatigue classifier on EEG data received from a dry-contact EEG electrode. Because the head-mountable devices can be worn in direct contact with a user's head, the device is advantageously proximate to various location at which an EEG electrode may be placed to record EEG data from specific regions of the user's brain. In addition, the dry-contact EEG electrode on the head-mountable device are convenient for users due in part to the ease of discrete uses in various environments.

Advantageously, the systems, methods, apparatuses, and devices of the present disclosure can detect fatigue before visible indicators appear on the user's face and/or in the user's body language. The approach disclosed herein can reduce the reduce a likelihood of a user losing focus (be, by detection and stimulation of the user to disrupt a degraded focus). In one aspect, this approach improves EEG technology by extending applicability of dry-electrodes in to practical settings which require mobility and robustness with respect to noise. In another aspect, this approach improves EEG technology by enabling a head-mountable device to determine brain function (e.g., detect fatigue) more accurately even in the presence of a poor-quality EEG data.

The systems, methods, apparatuses, and devices of the present disclosure can be applied to any activity involving long and monotonous tasks. Embodiments of the present disclosure be integrated into head-mounted device to provide vehicle drivers on long road trips with feedback based on their level of focus. For example, operators in transportation, such as drivers of cars, trains, boats, airplanes, and the like can benefit from such systems, methods, apparatuses, and devices. As an example, a head-mounted device comprises, e.g., a helmet (e.g., a helmet with virtual reality and/or augmented reality capabilities), a head band, headphones, eyeglasses and/or sun glasses (e.g., "smart" glasses), a cap, a visor, a headset (e.g., a microphone/speaker headset, a telephone headset). The head-mounted device can give feedback to and/or alert the user about their level of focus. As an example, a motorcycle helmet (implementing the approach of the present disclosure) can alerts the user when they are losing focus. In other examples, an application (implementing the approach of the present disclosure) is adapt to the user's metal state. For example, an application (e.g., a game) may change its look and feel of application (e.g., move parts of game to middle of a user's (estimated/ assumed) field of view) or move something from side to middle of a display (or vice versa) to force the user to move their eye position (i.e., to rouse the user).

The present disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples. This repetition is for the purpose of simplicity and clarity and does not, in itself, dictate a relationship between the various embodiments and/or configurations discussed.

Turning to FIG. 1, FIG. 1 illustrates a head-mountable device 102, according to some embodiments of the present disclosure. In this example, the head-mountable device 102 is a headband, which is attached to a head of a user to monitor activity of the user's brain. In some applications, the head-mountable device 102 prevents and/or reduces the likelihood of the user losing focus (for example, when performing a task that requires the user to focus for a long duration of time and/or requires infrequent interaction). The head-mountable device 102 comprises dry-contact EEG electrode 106a, dry-contact EEG electrode 106b, and a processor 104.

The dry-contact EEG electrodes 106a and 106b are placed at a location on the user's head that corresponds to the pre-frontal cortex of the user's brain. Thus, in operation, each of the dry-contact EEG electrodes 106a and 106b measures, in a time domain, EEG data corresponding to electrical activity of the pre-frontal cortex of the user's brain (i.e., pre-frontal cortex EEG data).

The processor 104 facilitates determining whether the user is fatigued based on the pre-frontal cortex EEG data from the dry-contact EEG electrodes. In some examples, the processor 104 is configured to process the EEG data (using spectral analysis) to determine whether the user is fatigued. In other examples, the processor 104 is configured to transmit the EEG data (and/or a representation of the EEG data) to another device (e.g., a server, a mobile device) and/or to receive data from the other device for the determination. The determination of whether or not the user is fatigued may couple to another system for recording and/or acting on the determination. For example, an output system may be activated (based on the determination) to rouse the user (by producing a sensory stimulation). A record (e.g. a data log) may store one or more indications of whether the user whether the user determined to be fatigued.

While the head-mountable device 102 of FIG. 1 is illustrated having two dry-contact EEG electrodes (each on the pre-frontal cortex), embodiments of the present disclosure are not limited to two electrodes. Other embodiments may include any number of electrodes. For example, FIG. 2 shows a head-mountable device having four dry-contact EEG electrodes.

Figure 2:
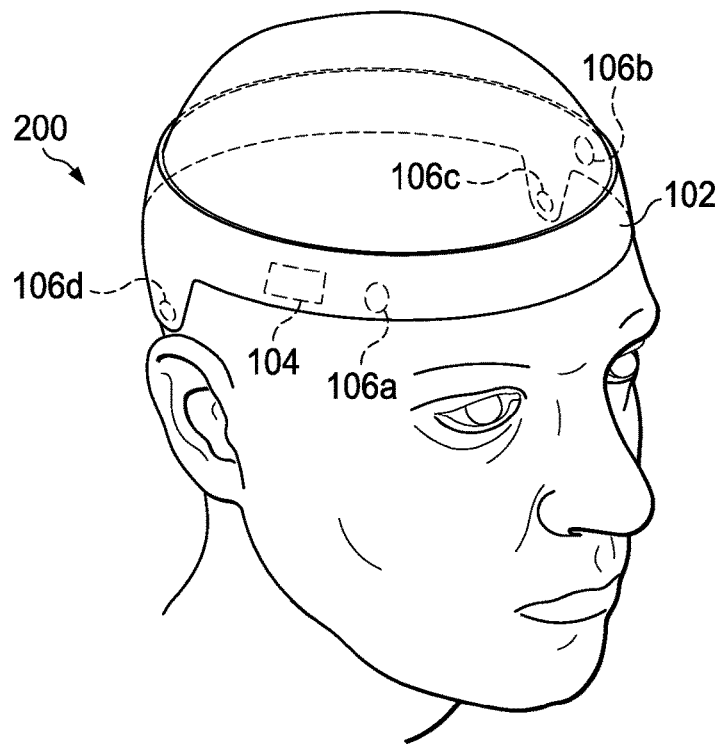

For example, FIG. 2 illustrates a further example of a head-mountable device 102. The head-mountable device 102 of FIG. 2 includes the components of FIG. 1 (i.e., processor 104, electrodes 106a and 106b) and two additional dry-contact EEG electrodes (i.e., electrodes 106c and 106d) for a total of at least four dry-contact EEG electrodes). The dry-contact EEG electrodes 106a and 106b measure pre-frontal cortex EEG data (e.g., as is described with respect to FIG. 1). The dry-contact EEG electrodes 106c and 106d are placed at a location on the user's head that corresponds to the temporal lobe of the user's brain. Thus, in operation, each of the dry-contact EEG electrodes 106c and 106d measures, in a time domain, EEG data corresponding to electrical activity of the temporal lobe of the user's brain (i.e., temporal lobe EEG data). The processor 104 facilitates determining whether the user is fatigued based on the pre-frontal cortex EEG data and the temporal lobe EEG data from the dry-contact EEG electrodes. It is noted that, in the present disclosure, one or more of the dry-contact EEG electrodes 106a, 106b, 106c, and 106d are sometimes referred to as an "electrode," "EEG electrode," or "dry-contact electrode" each of which refers to "dry-contact EEG electrode."

Figure 3:
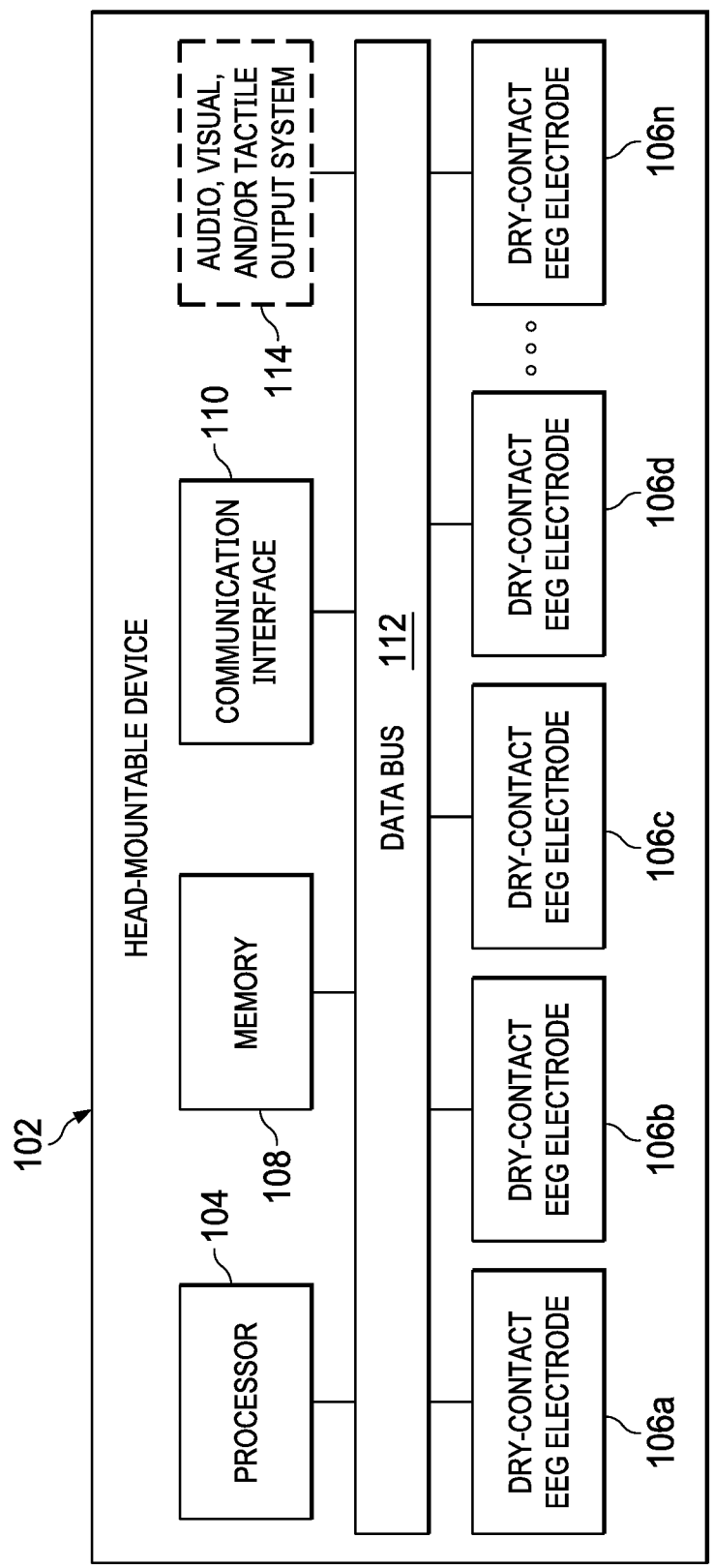

Several hardware components can facilitate a head-mountable device of the present disclosure (e.g., as illustrated in FIG. 1 and/or FIG. 2) using the EEG data to detect whether a user is fatigued (e.g., has lost focus needed for a particular task). For example, FIG. 3 is component diagram illustrating some hardware components. Many of the hardware components are not illustrated in other figures (e.g., FIGS. 1 and 2) only for simplicity of the figures. Each head-mountable device of the present disclosure includes a plurality of components to make the device operable to detect fatigue and/or to rouse a user that is determined to be fatigued. Thus, some examples of each of the head-mountable devices in other figures of the present disclosure include such hardware components (though the hardware components are not illustrated in the other figures, only for the sake of simplicity of the other figures).

Turning to FIG. 3, FIG. 3 is a simplified component diagram illustrating hardware components of a head-mountable device 102. The head-mountable device 102 comprises a processor 104, a memory 108, a communication interface 110, a set of dry-contact electrodes 106, and a data bus 112, which operably couples each of the other hardware components. In some examples, the head-mountable device 102 also comprises an audio, visual, and/or tactile output system 114 (the output system 114). The processor 104 is operable to execute one or more instructions to facilitate detecting whether a user has lost focus. The processor 104 may include one or more processor elements and is operably coupled to set of dry-contact electrodes 106.

The processor 104 is configured to access EEG data measured by the set of dry-contact electrodes 106, determine whether a user has lost focus based, at least in part, on the EEG data, and process the EEG data produced by the set of dry-contact electrodes 106. For example, the processor 104 may execute a Fourier transform on the EEG data to identify frequency data in various frequency bands, calculate features of the frequency data, and determine whether the user has lost focus based on the features. Alternatively, the processor 104 may transmit (e.g., using the communication interface 110) the EEG data itself and/or metadata of the EEG data (e.g., spectral features) to another device to make a determination and receive, from the device, a determination of whether the user has lost focus.

The memory 108 is operable to store data. Such data may any one or more of include: at least a portion of the EEG data generated from the dry-contact electrodes 106, a complete stream of data from each of the dry-contact electrodes, a time window of the EEG data produced from any one or more of the dry-contact electrodes; an indication of whether the EEG data corresponds to a loss of focus of the user; and/or code for execution by the processor. Such code can include: code that when executed operable to detect the loss of focus of the user. The code may include instructions corresponding to a classifier that is operable to receive input features and determine based on the input features one or more labels that correspond to a loss of focus. The code may be corresponding to a support vector machine classifier. The processor 104 may access the code from the 108 and/or from an external memory. The memory 108 includes one or more memory element.

The communication interface 110 is operable to communicate with other devices. The communication interface 110 may comprise a wireless transceiver (a wireless communication interface) and or wired communication interface for directly coupling to other devices. The communication interface may facilitate establishing wireless connections for example using a wireless communication protocols (such as Wi-Fi, Bluetooth, and the like). The communication interface 110 is configured to couple the head-mountable device to an output system. For example, the communication interface may include a wired transmission path to couple the head-mountable device 102 to an external output system (e.g., a vehicle screen speaker a light a gaming system. The communication interface 110 may support various communications and/or security protocols (e.g., Internet Protocol (IP), Hypertext Transfer Protocol (HTTP), Secure Sockets Layer (SSL), Simple Object Access Protocol (SOAP)). The communication interface 110 may include one or more communication interfaces.

The set of dry-contact electrodes 106 comprises dry-contact electrodes 106a, 106b, 106c, 106d, and . . . 106(n). Each of the dry-contact electrodes 106 is configured to measure, in a time domain, prefrontal cortex EEG data corresponding to electrical activity of the brain. The set of dry-contact electrodes 106 many include any number of electrodes (e.g., where electrode 106a is a first electrode, electrode 106b is a second electrode, electrode 106c is a third electrode, electrode 106d is a fourth electrode and electrode 106(n) is an n-th electrode. Because the EEG data produced by each of the dry-contact electrodes corresponds to and area of the brain proximate to where it is placed on the user head, it is important to know where each of the electrodes is placed to understand semantics of the EEG data. This issue of EEG placement is well-known and a standardized electrode placement is codified in the international 10-20 system.

The audio, visual, and/or tactile output system 114 (the output system 114) is operable to provide a sensory stimulation to the wearer of the head-mountable device 102. The output system 114 is operable to provide a sensory stimulation to a user based on detecting, from the EEG data, that the user has potentially lost focus. The output system 114 may comprise, e.g., a display screen to output a visible light (e.g., a message or icon) with corresponding speakers to put out an audible sound to rouse or wake the person if they are losing focus (e.g., by becoming drowsy or sleepy. The output system 114 may also comprise a tactile output system such as a vibratory component operative operable to produce a vibration that is perceptible to the user. When the output system 114 is embedded in the head-mountable device 102, the head mountable device itself may produce an audible sound, a visible light, and/and or a vibration to cause the user to pay attention and therefore draw their focus back on the task at hand. Such as sensory output may be used to tell the user that they have lost focus and, thereby encourage them to take action to regain focus.

FIG. 3 illustrates a specific number of each of head-mountable devices, processors, memory, communication interfaces, dry-contact electrodes, and output systems. However, any number of devices, processors, memory, communication interfaces, and electrodes may be implemented in a system according to one or more embodiments of the present specification.

The semantics of the EEG data produced by each of the dry-contact electrodes corresponds to an area of the brain, which in turn corresponds to a location at which each of the electrodes 106 is placed. Thus, the semantics of (and subsequent processing of) the EEG data from each electrode is linked to the location at which each of the electrode 106 is placed. A 10-10 system, which is described in further detail below, provides standard locations for placement of EEG electrodes. Each in the set of dry-contact electrodes 106 is placed at a location based on the 10-10 system.

Figure 4A:
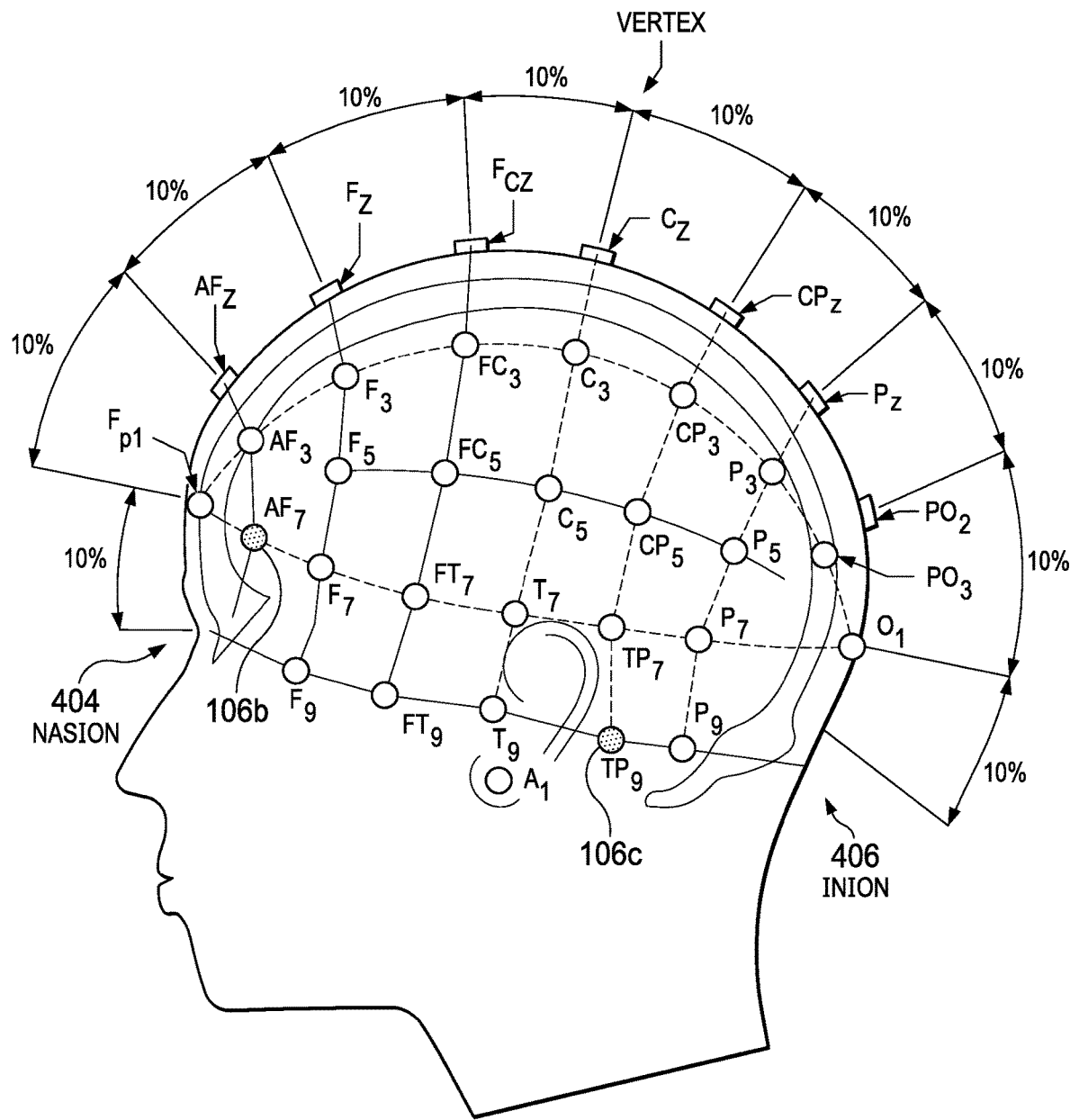
FIGS. 4A and 4B are simplified diagrams illustrating standard locations for EEG placement, according to some embodiments of the present disclosure
Figure 4B:
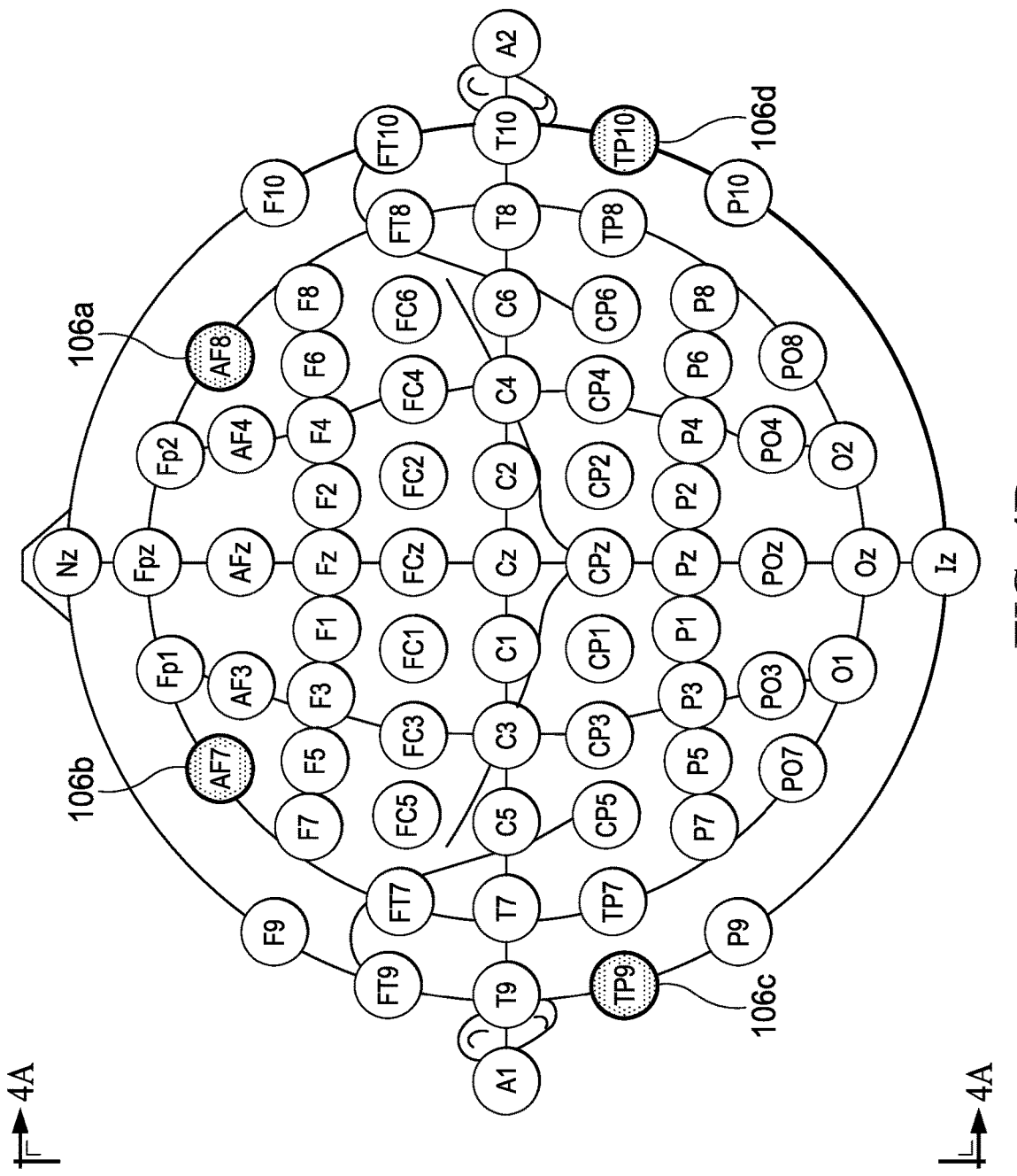

Turning to FIGS. 4A and 4B, FIGS. 4A and 4B are simplified diagrams illustrating standard locations for EEG placement. FIG. 4A illustrates a side view of an example head onto which the standard locations are mapped. FIG. 4B illustrates a top view of the example head onto which the standard locations are mapped. In FIG. 4B, an arrow labeled "FIG. 4A" generally indicates the viewpoint of the side view illustrated in FIG. 4A.

The American Clinical Neurophysiology Society (ACNP) publishes *Guidelines for Standard Electrode Position Nomenclature* (the "ACNP Guidelines"). In addition, the International Federation of Clinical Neurophysiology (IFCN) publishes the "IFCN Standards for Digital Recording of Clinical EEG" (the "IFCN Standard"). The ACNP Guidelines define a "10-10 system" and the IFCN Standard defines a "10% system" each of which is essentially equivalent to the other. Each of these standards adopts the standard locations as is displayed in the FIGS. 4A and 4B. In general, the standard locations are placed on along a grid, where lines of the grid are placed at about 10% intervals of a perimeter distance measured between naison 404 and inion 406. In the placement standards (i.e., the 10% system and the 10-10 system), each standard location is assigned a combination of letters and numbers to identify its position (e.g., "FP1," "F8," "TP9", "AF7"). The reference label in the FIGS. 4A and 4B match the combination of letters and numbers to identify assigned to each position.

Some classifiers (fatigue classifiers) of the present disclosure are "tuned" (e.g., by a training process) to detect spectral features of pre-frontal cortex EEG data and/or spectral features of a combination of pre-frontal cortex EEG data and temporal lobe EEG data. Thus, each electrode of the head-mountable devices (disclosed herein) are placed at (or approximately at) one of the standard locations corresponding to the pre-frontal cortex and/or the temporal lobe EEG data. The electrodes 106a and 106b are at standard locations corresponding to the pre-frontal cortex. In particular, the electrode 106a is the standard location assigned the designation of AF8; the electrode 106b is the standard location assigned the designation of AF7. The electrodes 106c and 106d are at standard locations corresponding to the temporal lobe. In particular, the electrode 106c is the standard location assigned the designation of TP9; the electrode 106d is the standard location assigned the designation of TP10.

A head-mountable device 102, when worn on a user's head, holds electrodes at the standard locations designation in FIGS. 4A and 4B (i.e., holds the electrodes 106a and 106b at AF8 and AF7, respectively; and, when applicable, holds the electrodes 106c and 106d at TP9 and TP10, respectively). A processor operably coupled to the head-mountable device 102 receives EEG data from the electrodes at the standard location and executes instructions that correspond to a process (e.g., logic) for indicating an estimate of a loss of focus. FIGS. 5, 7, 8, and 9 (which are discussed in further detail below) illustrate exemplary logic. The head-mountable device 102 may cause an output system to generate a sensory stimulation (e.g., a human-perceptible signal) based on data indicative of such an estimate (from the logic). FIG. 6 (which is discussed in further detail below) illustrates head-mountable device coupled to such an output system.

Figure 5:
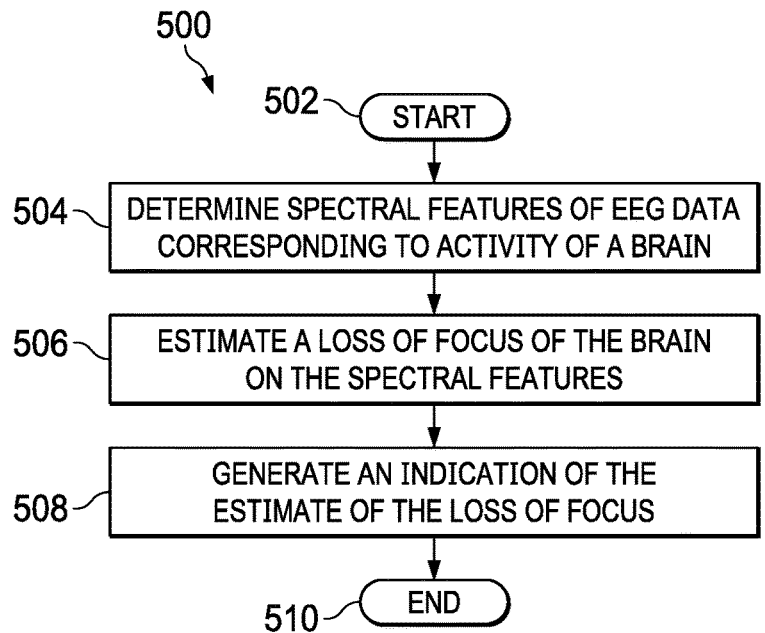
FIG. 5 illustrates logic for estimating whether a user has lost focus based on features of EEG data, according to some embodiments of the present disclosure.
Figure 6:
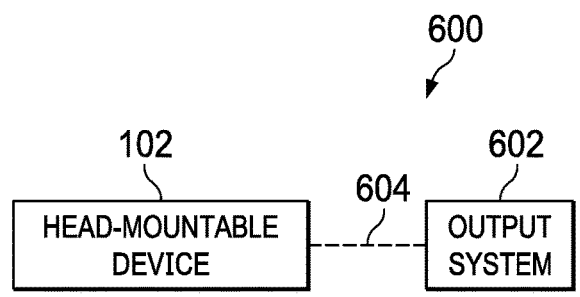
FIG. 6 illustrates a head-mountable device and an output system operably coupled by a connection, according to some embodiments of the present disclosure.

Turning to FIG. 5, FIG. 5 illustrates logic 500 for estimating whether a user has lost focus based on spectral features of EEG data. The logic 500 comprises: 502, initiate; 504, determine spectral features of EEG data corresponding to activity of a brain; 506, estimate a loss of focus of the brain based on the spectral features, and 508, generate an indication of the estimate of the loss of focus; and 510, end. The logic 500 may be executed by one or more processor (e.g., in a head-mountable device, server, or other device). What follows is a description of further details of the logic 500.

Logic 500 begins at 502, which may coincide with a start/end point of other logic, routines, and/or applications. The logic 500 advances from 502 to 504.

At 504, spectral features are determined (e.g., by the one or more processor) from EEG data; the EEG data corresponds to activity of a brain. The EEG data is a record of electrical activity (e.g. a voltage time-series) of the brain. In some examples, the determination includes receiving the spectral features from a device (e.g., a head-mountable device). The spectral features are derived from the EEG data using spectral analysis. In other examples, the determination includes calculating the spectral features directly from the EEG data. The logic 500 advances from 504 to 506.

At 506, a loss of focus of the brain is estimated (e.g., by the one or more processor) based on the spectral features. For example, the estimation may comprise detecting that the spectral features correspond to a loss of focus. The logic 500 advances from 506 to 508.

At 508, an indication of the estimate of the loss of focus is generated (e.g., by the one or more processor). The indication may comprise, e.g., a record of the estimate and/or a sensory stimulation (for output via an output system). The logic 500 advances from 508 to 510, at which the logic 500 ends.

In some embodiments, a head-mountable device executes the logic 500. In other embodiments, a remote processing device is in communication with, and remote from, a head-mountable device. In such an example, the remote processing device executes the logic 500 (e.g., based on receiving the spectral features and/or the EEG data from the head-mountable device). Alternatively, the remote processing device and the head-mountable device may cooperate to execute different portions of the logic 500 (e.g., in a client-server relationship). For example, a fatigue detection sever may execute the logic 500 (or implementations/examples thereof) based on receiving EEG data from a head-mountable device. Such a server may be implemented in a one location (e.g., a single device) or in multiple locations (e.g., distributed across multiple devices).

An output system may be activated based a detection of a loss of focus or an indication thereof (e.g., as is generated at 508 of FIG. 5). Turning to FIG. 6, FIG. 6 illustrates a system 600 in which a connection 604 operably couples a head-mountable device 102 and an output system 602.

The head-mountable device 102 (of FIG. 6) includes one or more dry-contact EEG electrodes for recording EEG data from a wearer's brain. The output system 602 is operable to generate a sensory stimulus (e.g., to stimulate the attention of the wearer). Each of the head-mountable device 102 and the output system 602 includes one or more communication interfaces to facilitate the connection 604.

The connection 604 is configured to carry signals between the head-mountable device 102 and the output system 602. For example, the connection 604 carries data transmitted from the head-mountable device 102 to the output system 602. The connection 604 may also carry data transmitted from the output system 602 to the head-mountable device 102. The connection 604 (of FIG. 6) can comprise a wired connection (e.g., established on one or more wires), a wireless connection (e.g., established on one or more radios), or both a wired and a wireless connection. The wired connection may utilize cables, plug/receptacle connectors (e.g., USB), or any other physical connection for data transmission established on one or more wires. The wireless connection may utilize wireless data transmission protocols (e.g., WI-FI protocol, BLUETOOTH protocol, a near-field communication (NFC) protocol, and the like) (e.g., established on one or more radios). The connection 604 can be direct or an indirect connection between the head-mountable device 102 and the output system 602. In a direct connection between the output system 602 (i.e., no intermediate device). When direct, the connection 604 excludes any intermediate device between the head-mountable device 102 and the output system 602. A BLUETOOTH connection established directly between the head-mountable device 102 and the output system 602 is an example of a direct connection. When indirect, the connection 604 includes intermediate device between the head-mountable device 102 and the output system 602. A network connection (e.g., established over the Internet) between the head-mountable device 102 and the output system 602 is an indirect connection at least because it utilizes various intermediate device (e.g., a server, a router, and the like) to facilitate the connection. As another example of an indirect connection, the head-mountable device 102 is indirectly connected to the output system 602 via a gaming system. The head-mountable device 102 may be coupled to the gaming system, which is, in turn, coupled to an audiovisual (A/V) output system (e.g., a television, a monitor, and the like).

Advantageously, the output system 602 can, e.g., rouse the wearer when they are drowsy by generating the sensory stimulus based on a data received from the head-mountable device (e.g., data indicating a loss of focus of the driver). Such sensory stimulus is particularly critical when the wearer is performing a task for which a loss of focus could result in bodily harm to themselves or another person or result in equipment damage.

The output system 602 is external to the head-mountable device 102. The output system 602 may be a stand-alone system. Alternatively, the output system 602 may be a component in another device such as a mobile device (e.g., a cell phone, a tablet, a gaming console, a laptop computer, and the like) or a vehicle (e.g., a motor vehicle, a locomotive, a railroad car, an aircraft, a velocipede, a motorcycle, and the like), or any other device. In other embodiments, an output system (e.g., output system 114 in FIG. 3) is onboard the head-mountable device 102.

The output system 602 is configured to generate a sensory stimulus. An output system may comprise any one or more of an audio output system (i.e., to output an audible sound), a visual output system (i.e., to output a visible light), and/or a tactile output system (i.e., to output a human-perceptible vibration). An audio output system is inclusive of a speaker. A visual output system is inclusive of a light (e.g., LED), a pixel, and/or a display screen (e.g., liquid crystal display (LCD) screen, a heads-up display, a monitor). A tactile output system is inclusive of a motor with a mass eccentrically located with respect to a drive shaft of the motor (i.e., to produce oscillatory vibrations when the motor is operated) or any other selectively vibrating hardware operable to produce a human-perceptible vibration. For example, a human-perceptible vibration can be, e.g., in a range of about 150-180 Hz.

The output system 602 can include any combination of audio output system, visual output system, and tactile output system. For example, the output system can include: (1) only the audio output system; (2) only the visual output system, (3) only the tactile output system, (4) only the audio output system and the visual output system (e.g., an audiovisual system), (5) only the audio output system and the tactile output system, (6) only the visual output system and the tactile output system, or (7) the audio output system, the visual output system, and the tactile output system.

The output system 602 is activated based (at least in part) on data received from the head-mountable device 102 over the connection 604. The output system 602 is configured to generate a sensory stimulus by outputting a human-perceptible signal. In some embodiments, the output system 602 generates the sensory stimulus based on a detection of a loss of focus and the sensory stimulus, advantageously, can rouse a user to increase focus. Such a human-perceptible signal may comprise an audible sound (i.e., in the audio frequency), a visible light (i.e., in the visible spectrum), and/or a human-perceptible vibration (e.g., in a range of about 150-180 Hz).

Figure 7:
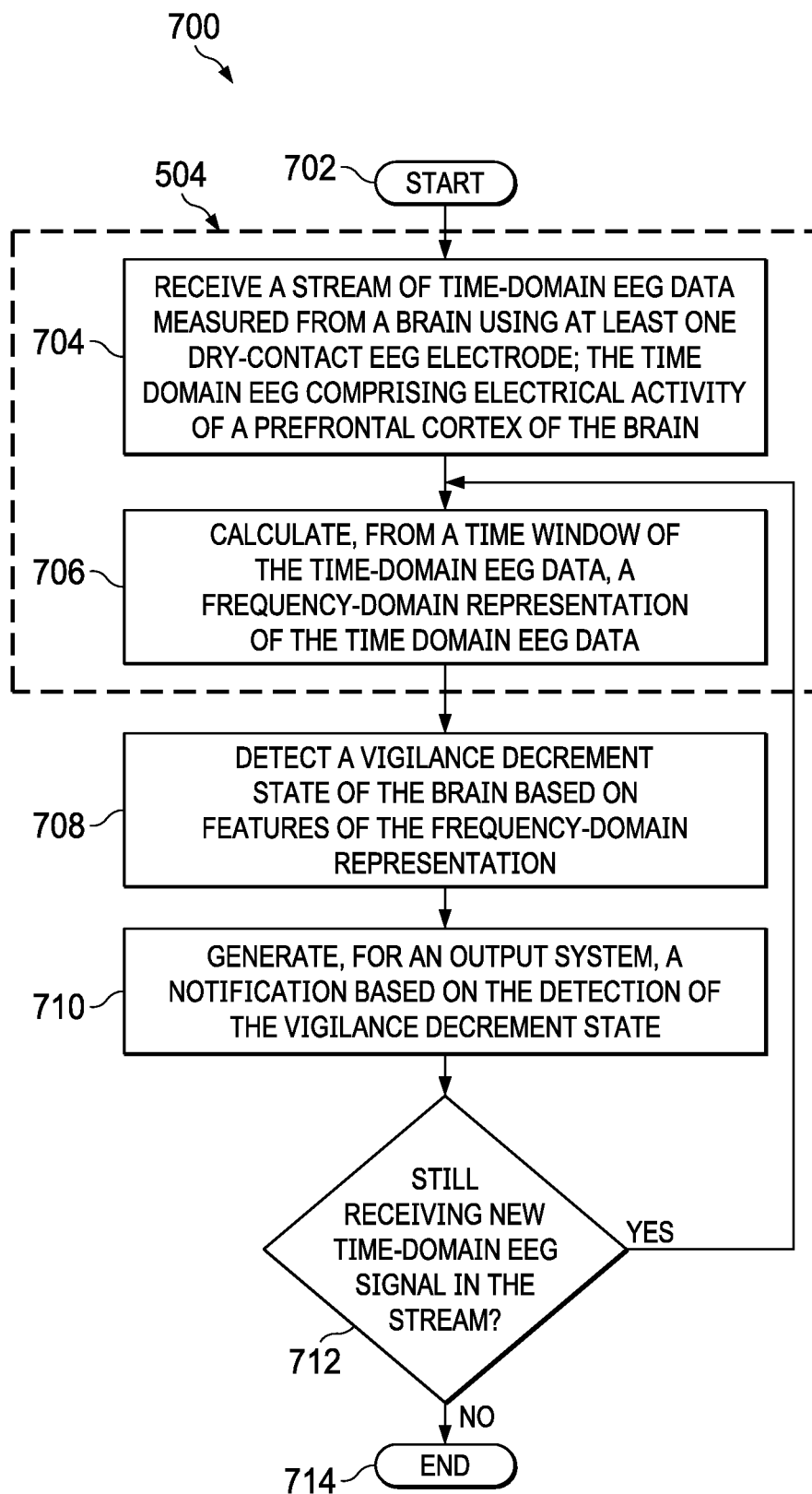
FIGS. 7 and 8 illustrate logic for estimating whether a brain is in a state of vigilance decrement based on electroencephalogram (EEG) data, according to some embodiments of the present disclosure.

Turning to FIG. 7, FIG. 7 illustrates logic 700 for estimating whether a brain is in a state of vigilance decrement. The logic 700 may be executed by one or more processor (e.g., in a head-mountable device, server, or other device). For example, the logic 700 may be stored on and executed by a head-mountable device to reduce a likelihood of a wearer of the device losing focus (e.g., becoming drowsy or otherwise distracted). The logic 700 comprises 702, 704, 706, 708, 710, 712, and 714 as is described in further detail below.

The logic 700 begins at 702, which may coincide with a start/end point of other logic, routines, and/or applications. The logic 700 advances from 702 to 704.

At 704, a stream of time-domain EEG data is received. The time-domain EEG data is measured from a brain using at least one dry-contact EEG electrode. The time-domain EEG comprises electrical activity of a prefrontal cortex of the brain (e.g., recorded as amplitude of voltage that varies with respect to time). The at least one dry-contact EEG electrode may be placed at a location on a head that corresponds to the prefrontal cortex of the brain. In some embodiments, the at least one dry-contact EEG electrode comprises two dry-contact EEG electrodes to record data from the prefrontal cortex of the brain; a first placed at AF7 and a second placed at AF8 of the placement standards. In other embodiments, the at least one dry-contact EEG electrode comprises four dry-contact EEG electrodes to record data from the prefrontal cortex of the brain and from the temporal lobe of the brain; a first at placed at AF7, a second placed at AF8, a third at placed at TP9, a fourth placed at TP10 of the placement standards. The logic 700 advances from 704 to 706.

At 706, a frequency-domain representation of the time-domain EEG data is calculated from a time window of the time-domain EEG data. The time window is a discrete slice of time from the data stream. In some examples, only the time window is stored (e.g., in a circular buffer) and the entire stream is not stored to reduce the storage requirements of the head-mountable device. Time window is back-sampled from a current time (or most recent data point) in the stream. The frequency-domain representation is used to identify characteristics of the signal that are indicative of loss of focus of the user. The logic 700 advances from 706 to 708.

At 708, detect a vigilance decrement state of the brain based on features of the frequency-domain representation. The vigilance decrement state comprises a state of EEG data that corresponds to a loss of focus of the user as indicated by the user's reaction times (or predicted reaction times) in response to a stimulus. For example, when the user's reaction time is (or is predicted to be based on EEG data) greater than or equal to the threshold, the user is determined to be in the vigilance decrement state (i.e., has lost focus). When the user's reaction time is (or is predicted to be based on EEG data) less than the threshold, the user is determined to not be in the vigilance decrement state (i.e., has not lost focus). An indication of whether the vigilance decrement state is detected, e.g., true (e.g., vigilance decrement state is detected; i.e., the user has lost focus) or false (e.g., vigilance decrement state is not detected; i.e., the user has not lost focus). The features are indicative of a loss of focus of the user (based on the EEG data recorded from the user's brain). The logic 700 advances from 708 to 710.

At 710, a notification is generated for an output system. The notification is generated based on the detection of the vigilance decrement state (i.e., at 708). The notification may be set to last for a specific period of time (regardless of how long the vigilance decrement state lasts). In one example, the output comprises a sensor stimulation (e.g., a human perceptible signal). The logic 700 advances from 710 to 712.

At 712, determine whether new time-domain EEG data is still received in the stream (i.e., is the stream generating new EEG data?). The logic 700 advances from 712 back to 706 based on a determination that new time-domain EEG data is received via the stream (e.g., the time window is advanced by a unit of time to get new data in the time window). The logic 700 advances from 712 to 714 based on a determination that no new time-domain EEG data is received via the stream.

The logic 700 ends at 714, which may coincide with a start/end point of other logic, routines, and/or applications.

Figure 8:
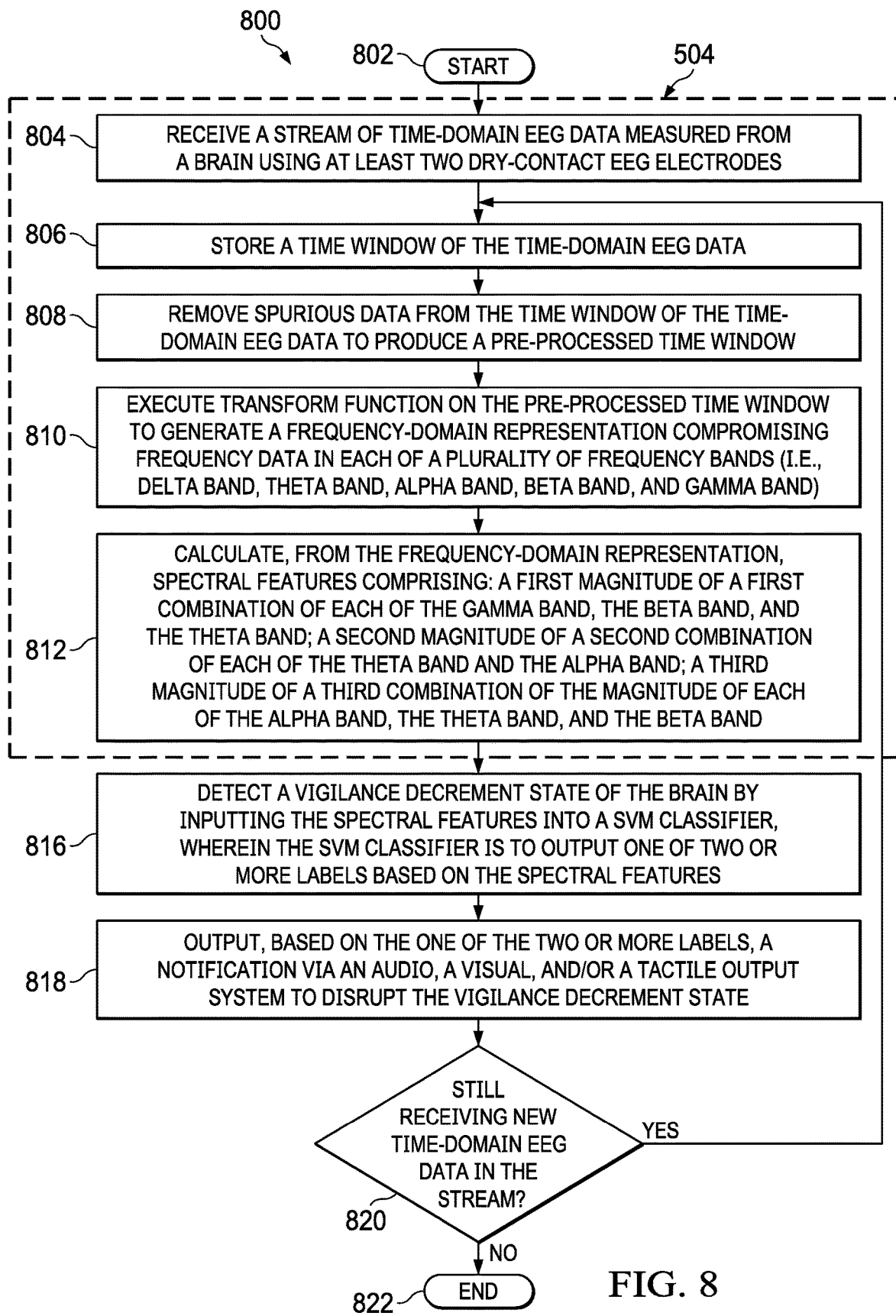

The logic 700 is an implementation of the logic 500. In particular, with respect to FIGS. 5 and 7: 504 corresponds to 704 and 706, 506 corresponds to 708, and 508 corresponds to 710. The present disclosure is not limited to such an example. FIG. 8 illustrates another implementation of the logic 500.

Turning to FIG. 8, FIG. 8 illustrates a logic 800 for estimating whether a brain is in a state of vigilance decrement. The logic 800 may be executed by one or more processor (e.g., in a head-mountable device, server, or other device). The logic 800 comprises 802, 804, 806, 808, 810, 812, 816, 818, 820, and 822 as is described in further detail below.

The logic 800 begins at 802, which may coincide with a start/end point of other logic, routines, and/or applications. The logic 800 advances from 802 to 804.

At 804, receive a stream of time-domain EEG data measured from a brain using at least two dry-contact EEG electrodes. The EEG data may be received directly or indirectly from the at least two dry-contact EEG electrodes. Each of the at least two dry-contact EEG electrodes measures the EEG data in the time domain (e.g., the EEG data comprises an amplitude that varies with respect to time).

A head-mountable device can hold the dry-contact EEG electrodes a location corresponding to a prefrontal cortex of the brain. For example, the at least two dry-contact EEG electrodes may be placed at standard locations AF7 and AF8 (based on the 10-10 system's standard for EEG placement) on a user's head. In some examples, the at least two dry-contact EEG electrodes further include a second pair of dry-contact EEG electrodes to measure temporal lobe EEG data corresponding to activity of a temporal lobe of the brain. In such examples, the head-mountable device can hold the second pair of dry-contact EEG electrodes a location corresponding to the temporal lobe of the brain. For example, the at least two dry-contact EEG electrodes may be placed at standard locations TP9 and TP10 (based on the 10-10 system's standard for EEG placement) on a user's head.

At 806, store a time window of the time-domain EEG data. The time window of the time-domain EEG data may be stored in a memory.

Figure 9:
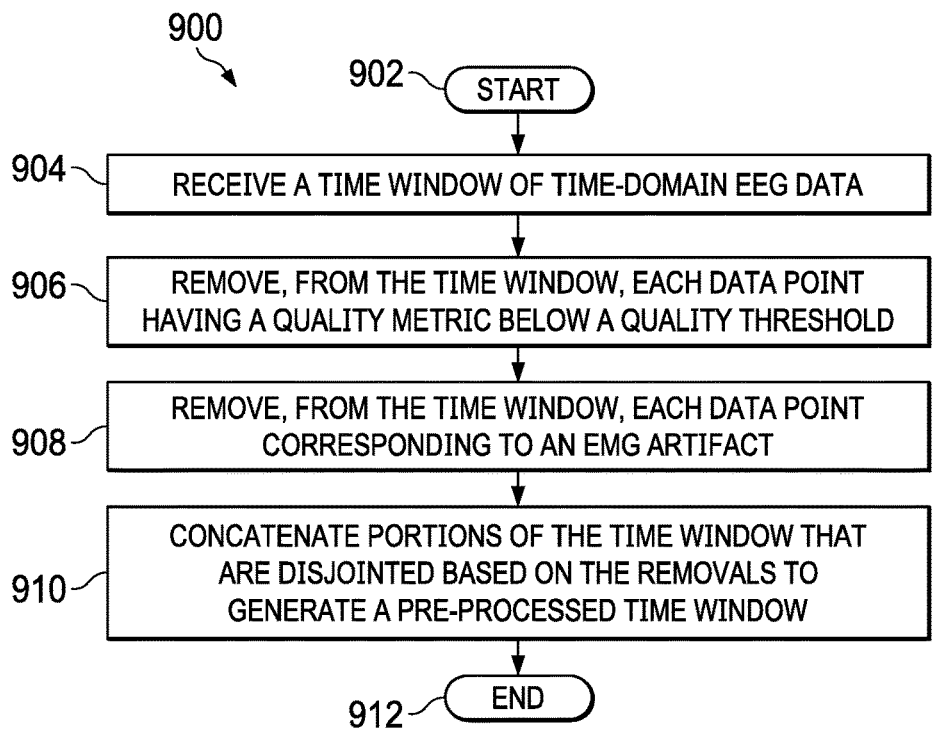
FIG. 9 illustrates logic for removing spurious data from a time window of the time-domain EEG data, according to some embodiments of the present disclosure.

At 808, remove spurious data from the time window of the time-domain EEG data to produce a pre-processed time window. Such removal can clean-up the EEG data and/or discard data that does not meet a threshold (e.g., quality and/or noise threshold). The logic 900 of FIG. 9, is an example of such a removal. The removal can result in the pre-processed time window being shortened (truncated) relative to the original time window.

At 810, execute transform function on the pre-processed time window to generate a frequency-domain representation, the frequency domain representation comprising frequency data for the EEG data in each of a plurality of frequency bands (i.e., a delta band, a theta band, an alpha band, a beta band, and a gamma band). The transform function may include a Fourier Transform (e.g., a Fast Fourier Transform (FFT)). The theta band is centered at about 6 hertz; the alpha band is centered at about 12 hertz; the beta band is centered at about 23 hertz; and gamma band is centered at about 40 hertz. As a further example, the theta band can comprise frequencies x1, where 4 Hz≤x1<8 Hz; the alpha band can comprise frequencies x2, where 8 Hz≤x2<16 Hz; the beta band can comprise frequencies x3, where 16 Hz≤x3<30 Hz; and the gamma band can comprise frequencies x4, where 30 Hz≤x4<50 Hz.

At 812, spectral features are calculated from the frequency-domain representations. The spectral features comprise: a first magnitude of a first combination (f1) of each of the gamma band, the beta band, and the theta band; a second magnitude of a second combination (f2) of each of the theta band and the alpha band; and a third magnitude of a third combination (f3) of each of the alpha band, the theta band, and the beta band. As an example, the first combination can comprise a first function of (the gamma band+the beta band)/the theta band; the second combination can comprise a second function of the theta band/the alpha band, and the third combination can comprise a third function of (the alpha band+the theta band)/the beta band. Thus, in examples where there are two EEG electrodes, then six features are calculated (i.e., three for each of the two signals for a total of six). In examples where there are EEG electrodes, then 12 features are calculated (i.e., three for each of the four signals for a total of 12). As an illustrative example, the spectral features may include an area under the curve of a corresponding function (i.e., of f1, f2, or f3). The area may be calculated by integrating the function.

Figure 13:
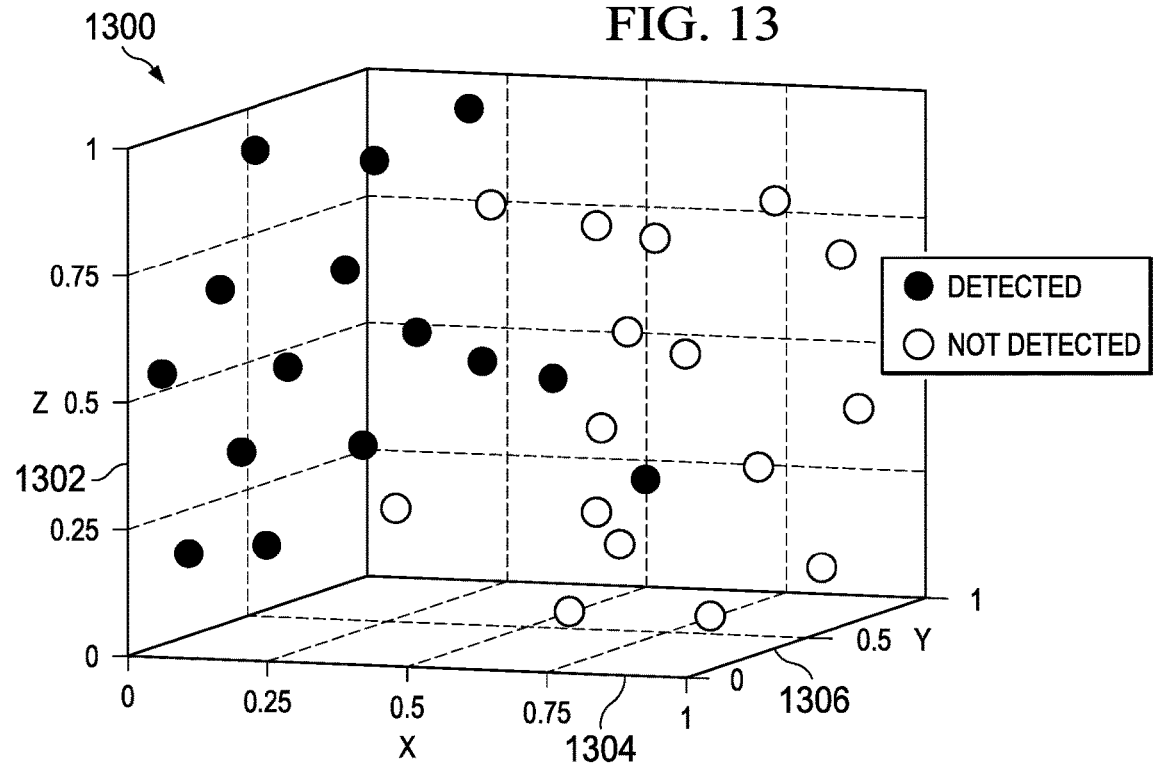
FIGS. 13 and 14, illustrate an example of training a classifier and subsequent decision making by the classifier after training, according to some embodiments of the present disclosure.

At 816, detect a vigilance decrement state of the brain by inputting the spectral features into a SVM classifier, wherein the SVM classifier is to output one of two or more labels based on the spectral features. The SVM has been trained by running a training routine on labeled examples; the labeled examples include a set of features where each in the set associated with a labeled (e.g., a vigilance decrement "detected" label and a vigilance decrement "not detected" label) (e.g., as is shown in FIG. 13). A dimensionality of a hyperspace utilized by the SVM classifier is equal to the number of features. Thus, a single electrode would produce 3 features (i.e., one for each of f1, f2, and f3, above), and the SVM classifier would plot it in a 3-dimensional space. Likewise, two EEG electrodes would produce six features and the SVM classifier would plot them in a 6-dimensional space. Similarly, four EEG electrodes would produce 12 features and the SVM classifier would plot them in a 12-dimensional space. In general, the number of features (n) results in the SVM plotting them in a n-dimensional space.

At 818, output, based on the one of the two or more labels, a notification via an audio, a visual, and/or a tactile output system to disrupt the vigilance decrement state. The output system coupled to the head-mountable by a communication interface. In some examples, the output system is onboard a head-mountable device. In other examples, is external to the head-mountable device. For example, the output system may be located in a vehicle (e.g., a motor vehicle, a locomotive, a railroad car, an aircraft, a velocipede, and a motorcycle) or in a gaming coupled to an audiovisual device.

The notification results in a sensory stimulation, e.g., to rouse the user. For example, the notification may be comprised in a component of a graphical user interface. The sensory stimulation comprises an audible sound, a visible light, and/or a vibration. The audio output system is configured to output the audible sound, the visual output system is configured to output the visible light, and the tactile output system is configured to output the vibration. The output system may comprise an audiovisual system configured to output the audible sound and the visible light.

At 820, determine whether new time-domain EEG data is still received in the stream (i.e., Is the stream generating new EEG data?). The logic 800 advances from 820 back to 806 based on a determination that new time-domain EEG data is received via the stream (i.e., using new data from advancing the time window). The logic 800 advances from 820 to 822 based on a determination that no new time-domain EEG data is received via the stream.

The logic 800 ends at 822, which may coincide with a start/end point of other logic, routines, and/or applications.

The logic 800 is an implementation of the logic 500. In particular, with respect to FIGS. 5 and 8: 504 corresponds to 804, 806, 808, 810, and 812, 506 corresponds to 816, and 508 corresponds to 818. The present disclosure is not limited to such an example.

Turning to FIG. 9, FIG. 9 illustrates logic 900 for removing spurious data from a time window of the time-domain EEG data. The logic 900 may be executed by one or more processor (e.g., in a head-mountable device, server, or other device). The logic 900 is a non-limiting example of 808 of FIG. 8. The logic 900 comprises 902, 904, 906, 908, 910, and 912, as is described in further detail below.

The logic 900 begins at 902, which may coincide with a start/end point of other logic, routines, and/or applications. The logic 900 advances from 902 to 904.

At 904, receive a time window of time-domain EEG data. The EEG data may be a time window of data that is being analyzed to determine (or predict) whether a user (from which the data was measured) is fatigued.

At 906, remove, from the time window, each data point having a metric below a threshold. For example, all data having a quality metric below a quality threshold (e.g., a noise threshold) may be deleted. A dry-contact EEG electrode may have an impedance of 100 kΩ or more. In some examples, the removal comprises delete at least one sub-window of the time window in which the EEG data deviates from the noise floor (e.g., a moving average of noise) of the dry-contact EEG electrode.

At 908, remove, from the time window, each data point corresponding to an electromyogenic (EMG) artifact. EMG artifacts can be produced, e.g., when a user blinks their eyes, frowns, or moves other muscles nearby a dry-contact electrode. Such artifacts can have, e.g., 100× the magnitude of EEG data from the brain and therefore can overshadow the EEG signal when present. Consequently, the artifacts are removed to At 910 concatenate portions of the time window that are disjointed based on the removals to generate a pre-processed time window. For example, disjointed sub-windows created by removal of artifacts or poor-quality data are concatenated to produce the pre-processed time window, which is a truncated time window of the original time window (as received at 904) of the EEG data.

The logic 900 ends at 912, which may coincide with a start/end point of other logic, routines, and/or application.

The logic 900 is a non-limiting example of 808 of FIG. 8. The logic 900 removes noisy data and is able to extract usable data from the EEG data. Advantageously, the logic 900 can output usable information even when given poor quality EEG data as input.

FIGS. 10A, 10B, 10C, 11A, 11B, 12, 13, and 14 are described in the context of an example execution of logic for transforming EEG data from a time-domain to frequency domain to detect a loss of focus. For example, the head-mountable device 300 (of FIG. 3) executing the logic 800 (of FIG. 3) on a stream of time domain EEG data.

Figure 10A:
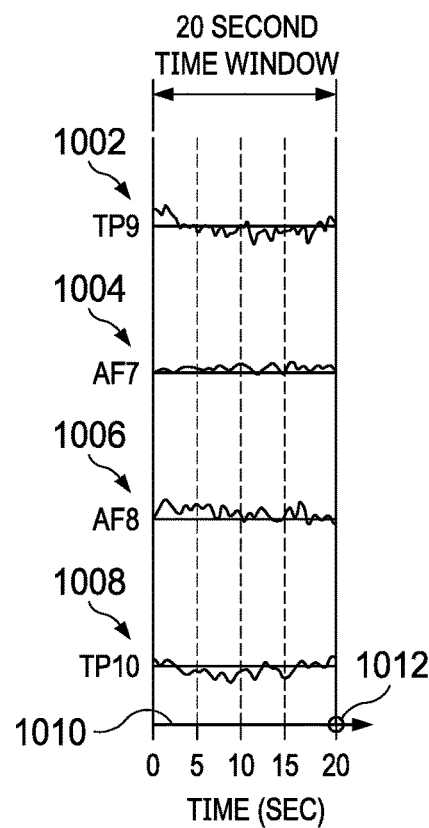
FIGS. 10A, 10B, and 10C illustrate progression of a stream of time domain EEG data, according to some embodiments of the present disclosure.
Figure 10B:
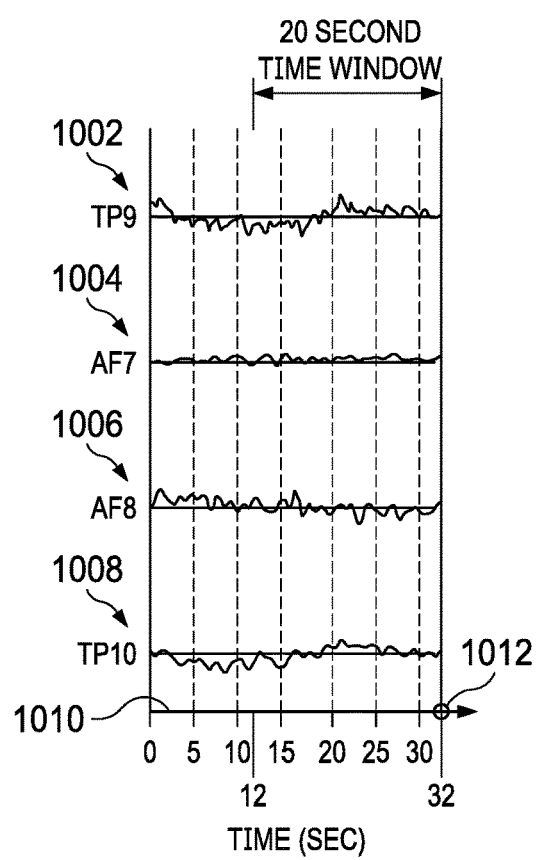
Figure 10C:
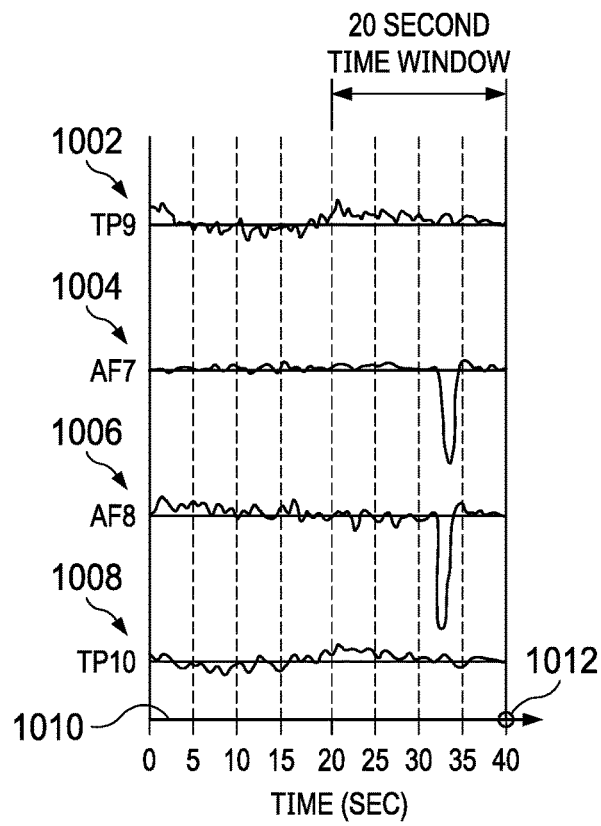

Turning to FIGS. 10A, 10B, and 10C, FIGS. 10A, 10B, and 10C illustrate progression of a stream of time domain EEG data (i.e., a data stream). The data stream includes EEG data recorded from four EEG electrodes, each of which is placed that a standard location on a user's head (i.e., in this case, standard locations AF7, AF8, TP9, and TP10). The EEG data includes a time series of voltage measurements measured by a corresponding EEG electrodes. The data stream progresses from a starting point of the data stream (e.g., a time zero in the data stream) to a first time in the data stream (i.e., as illustrated in FIG. 10A), from the first time to a second time in the data stream (i.e., as illustrated in FIG. 10B), and from the second time to a third time in the data stream (i.e., as illustrated in FIG. 10C).

Each of the FIGS. 10A, 10B, and 10C illustrates four graphs (i.e., the graphs 1002, 1004, 1006, and 1008) corresponding to the EEG data recorded from the four EEG electrodes. Each graph is a plot of the EEG data with respect to time. A horizontal axis corresponds to time (measured in seconds) relative to the starting point of the data stream. A vertical axis corresponds to a voltage. The graph 1002 is a plot of EEG data recorded from an EEG electrode placed the standard location TP9 (e.g., electrode 106c). The graph 1004 is a plot of EEG data recorded from an EEG electrode placed the standard location AF7 (e.g., electrode 106b). The graph 1006 plots EEG data recorded from an EEG electrode placed the standard location AF8 (e.g., electrode 106a). The graph 1008 plots EEG data recorded from an EEG electrode placed the standard location TP10 (e.g., electrode 106d). The axis 1010 consolidates time labels for the horizontal (time) axis of each of the graphs. As the time progresses, a marker 1012 indicates the "current" time in each Figure. As the data stream progresses in time, a marker 1012 indicates the "current" time in each of the FIGS. 10A, 10B, and 10C. The systems and methods of the present disclosure advantageously identify, based on variations in the EEG data (e.g., voltages) over time, whether a user (whose brain is being monitored) is fatigued.

Turning to FIG. 10A, FIG. 10A illustrates the data stream at the first time. The first time is about 20 seconds into the data stream (as generally indicated by the marker 1012 in FIG. 10A). A time window is selected from the data stream for analysis. The time window is parsed or otherwise retrieved from the data stream. Any size of time window may be utilized without departing from the scope of the present disclosure. The time window should include sufficient EEG data upon which to make a determination that is statistically significant a basis for analysis. An excessively long time-window may result in slow performance of a hardware (e.g., memory, processor) and, therefore, limit applicability of the analysis in cases where a decision is needed in instantaneously (e.g., real-time, or near real-time). Either the entire stream or be time window (or both) are stored in a memory for example memory 108 (of FIG. 3) or in a remote/external memory. In this example, the time window is a 20-second duration of time. The time window is back-sampled relative to the current time of 20 seconds in the data stream (i.e. from about 0 seconds through about 20 seconds of the data stream).

The analysis (e.g., using the logic 800 of FIG. 8) determines whether a user (from which the EEG is being collected) is fatigued. The analysis processes the EEG data in the 20 second time window of the data stream. In this example, the determination is made while the user is actively performing a task (e.g., executed in real-time (or near real-time)). Alternatively, the determination may be made after the user has ended the task (i.e., on previously recorded data). The determination can be made at from time to time (e.g., based on detecting certain events, at regular intervals of time, and/or at pseudo-random intervals of time). The determination can be stored and/or transferred to another system. For example, periodically recorded data indicative of whether the user is determined to be fatigued or not may be stored in a log (e.g., for later review and/or processing). An instantaneous determination may be transferred to an alert system (e.g., to alert the user and/or to alert a manager of the user) or to a control system (e.g., to disable equipment if the user (while operating the equipment) is determined to be impaired (e.g., due to being drowsy or nearly asleep)).

In the example of FIG. 10A, it is determined (based on the analysis of the EEG data collected at the first time) that the user is not fatigued (e.g., spectral features of the signal in the time window do not correspond to a vigilant decorative state). The determined that the user is not fatigued may be stored in a memory (with a timestamp corresponding to the first time) of a head-mountable device and/or transmitted to another system. The EEG electrodes continue producing the data stream and reach the second time.

Turning to FIG. 10B, FIG. 10B illustrates the data stream at the second time. The second time is about 32 seconds into the data stream (as generally indicated by the marker 1012 in FIG. 10B). The time window is selected from the data stream for analysis. At the second time, the time window include EEG data contained in the last 20 seconds of the data stream (i.e., from about 12 seconds through about 32 seconds of the data stream). Again, the analysis determines whether the user is fatigued. In the example of FIG. 10B, it is determined (based on the analysis of the EEG data collected at the second time) that the user is not fatigued. based on a determination that the spectral features of the signal in the time window do not correspond to a vigilant decorative state. Again, the determined that the user is not fatigued may be stored in a memory (with a timestamp corresponding to the second time) of a head-mountable device and/or transmitted to another system. The EEG electrodes continue producing the data stream and reach the second time.

Turning to FIG. 10C, FIG. 10C illustrates the data stream at the third time. The third time is about 40 seconds into the data stream (as generally indicated by the marker 1012 in FIG. 10C). The time window is selected from the data stream for analysis. At the third time, the time window include EEG data contained in the last 20 seconds of the data stream (i.e., from about 20 seconds through about 40 seconds of the data stream). Note that each of the graphs 1004 and 1002 includes a distinct spike in the EEG produced from the electrodes at AF7 and AF8. Again, the analysis determines (based on the analysis of the EEG data collected at the third time) whether the user is fatigued. As an example of a portion of the analysis, FIGS. 11A and 11B illustrate results of an example pre-processing of the 20-second time window of the data stream time (i.e., from about 20 seconds through about 40 seconds of the data stream).

Figure 11A:
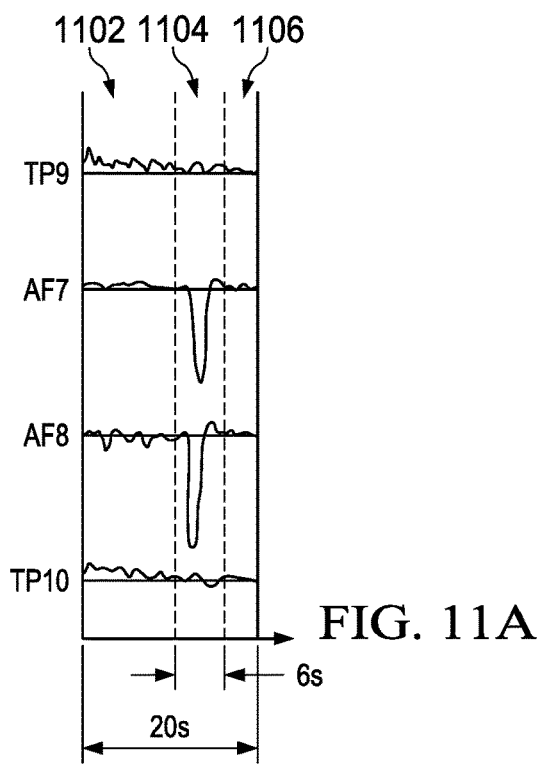
FIG. 11A illustrates a time window of the stream of time domain EEG data from the FIG. 10C.

Turning to FIG. 11A, FIG. 11A illustrates the 20-second time window of the data stream from the FIG. 10C. The data are processed (e.g., using the logic 900 of FIG. 9) to remove spurious data. The processing split the time window into sub-windows 1102, 1104, and 1106. In particular, the processing identified, within the time window, spurious data and created the sub-window 1104 (i.e., a 6-second sub-window) to mark the boundary of the spurious data. The spurious data are identified based on the deviation from the other EEG data in the signal (e.g., relative to a moving average, or relative to an estimate of background noise inherent in the data produced by a corresponding EEG electrode, a noise floor of the EEG electrode). In this case, the spurious data corresponds to a muscle artifact produced by the user blinking their eyes (e.g., an eye-blink artifact) and is orders of magnitude larger than the data present in the rest of the signal. The processing removes the spurious data (the sub-window 1104, 6-second long) from the time window (20 second time window) to produce a truncated version of the time window (i.e., a 14-second time window).

Figure 11B:
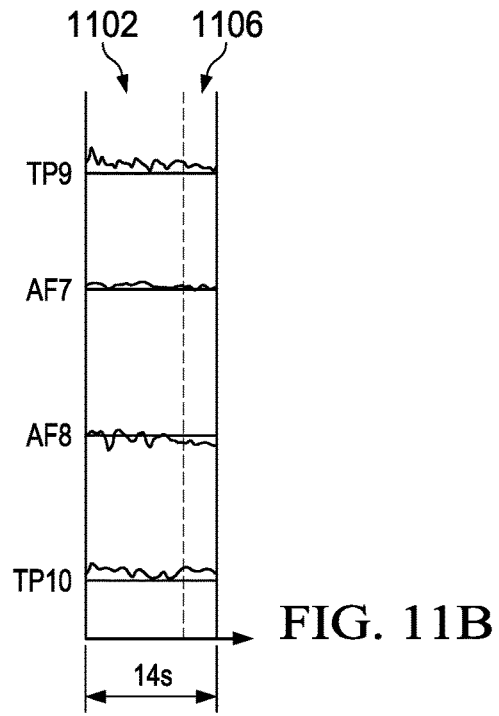
FIG. 11B illustrates a truncated version of the time window from FIG. 11A.

Turning to FIG. 11B, FIG. 11B illustrates a truncated version of the time window from FIG. 11A. Because a 6 second sub-window of spurious data was removed from the original 20 second time window, the truncated version of the time window is about 14 seconds long. The truncated time window of FIG. 11B is then processed to remove spurious data (i.e., pre-processed). At this point it is ready for further processing to detect features and maybe indicative of the vigilance of a loss of focus by detecting based on the detection of the digital decrements.

Time windows are periodically sampled from the data stream. Suring pre-processing, the amount of spurious data removed from a particular time-window can vary relative to other time windows from the same data stream. In the example of FIGS. 11A and 11B, six seconds of spurious data were removed from the 20 second time window, which resulted in the 14 second truncated time window. Time windows sampled at other time points in the data stream may remove less spurious data, resulting in a longer truncated time window or may remove more spurious data, resulting in a shorter truncated time window. Moreover, in some cases no spurious data is removed, which would result in a truncated time window that is equal in length to the original time window (i.e., no truncation required). Thus, such pre-processing can result in in truncated time windows of various sizes. Similar data is produced for each channel of data produced in the stream of EEG data.

A Fourier transform, for example, a Fast Fourier transform (FFT) is applied to the data stream from the truncated time window of FIG. 11B (i.e., the EEG data for each of TP9, AF7, AF8, and TP9), to generate one or more frequency domain representations of the data stream. The FFT transforms the EEG data from the time domain to the frequency domain representation by decomposing the EEG data into particular frequency bands that are of interest for detecting fatigue.

A Fourier transform, for example a Fast Fourier transform (FFT) is applied to the AF7 EEG data from the truncated time window of FIG. 11B (i.e., pre-processed EEG data), to generate a frequency domain representation. The FFT transforms the pre-processed EEG data from the time domain to the frequency domain representation by decomposing the pre-processed EEG data into particular frequency bands that are of interest for detecting fatigue. Showing Graphically showing frequency domain representations for all of the EEG data channels TP9, AF7, AF8, and TP9 could be complicate the Figures. Thus, only for the sake of simplicity of the figures, FIG. 12 illustrates a frequency domain representation of the AF7 EEG data from the truncated time window. However, the FFT can produce a corresponding frequency domain representation for EEG data from each of TP9, AF8, and TP9 (in addition to that for the AF7 EEG data).

Turning to FIG. 12, FIG. 12 illustrates a frequency domain representation 1200 of the AF7 EEG data from the truncated time window of FIG. 11B (i.e., pre-processed EEG data), functions 1210 (f1, f2, and f3), and a classifier 1212. Each of the functions 1210 is derived from the frequency domain representation 1200. The functions include:

$$f1(t) = \frac{\text{gamma}(t) + \text{beta}(t)}{\text{theta}(t)} \quad \text{Equation 1}$$

$$f2(t) = \frac{\text{theta}(t)}{\text{alpha}(t)} \quad \text{Equation 2}$$

$$f3(t) = \frac{\text{alpha}(t) + \text{theta}(t)}{\text{beta}(t)} \qquad \text{Equation 3}$$

Features f1', f2', and f3' are derived from the functions f1, f2, and f3 respectively. Each of the features f1', f2', and f3' can be any mathematical quantity derived from the corresponding function. The features f1', f2', and f3' are input to a classifier 1212. The classifier 1212 outputs a classification based, at least in part, on the features f1', f2', and f3'.

The frequency domain representation 1200 is a decomposition of the pre-processed EEG data into frequencies in each of a plurality of frequency bands. For Example, an FFT is applied to the pre-processed EEG data from to decompose in into frequencies in each of the frequency bands. The frequency domain representation, as illustrated in FIG. 12, includes four graphs (i.e., the graphs 1202, 1204, 1206, and 1208) corresponding to each of the frequency bands. Each graph is a plot of frequency domain data in its corresponding frequency band for the pre-processed EEG data. A length of each graph matches that of the pre-processed EEG data, which in this case corresponds to 14 seconds of data. Each graph describes how the frequency content (energy in each of the frequency bands) varies with time.

The frequency bands include a theta band, an alpha band, a beta band, and a gamma band. Each of the frequency bands covers a range of frequencies centered about a particular frequency. The theta band is a frequency band is centered at about 6 Hz. In a particular example, the theta band comprises a range from about 4 Hz to about 8 Hz. The alpha band is a frequency band is centered at about 12 Hz. In a particular example, the alpha band comprises a range from about 8 Hz to about 16 Hz. The beta band is a frequency band is centered at about 23 Hz. In a particular example, the beta band is a range from about 16 Hz to about 30 Hz. The gamma band is a frequency band is centered at about 40 Hz. In a particular example, the gamma band is a range from about 30 Hz to about 50 Hz.

The frequency domain representation 1200 is used to determine features indicative of fatigue (i.e., the features f1', f2', and f3'). Each of the functions 1210 (f1, f2, and f3) is a combination of a frequency domain data (plotted as functions of time (t)) from two or more bands in the frequency domain representation 1200. The function f1(t) is combination of the gamma band (Gamma(t)), the beta band (Beta(t)), and the theta band (Theta(t)). The function f1 is a combination of frequency data in each of the gamma frequency, the beta frequency, and the theta frequency. The function f2(t) is combination of theta band (Theta(t)) and the alpha band (Alpha(t)). The function f2 is a combination of frequency data in each of the theta frequency and the alpha frequency. The function f3 is a combination of frequency data in each of the theta band (Theta(t)), the alpha band (Alpha(t)), and the beta band (Beta(t)).

Features f1', f2', and f3' (spectral features) are derived from the functions f1, f2, and f3 respectively of FIG. 12. These spectral features are mathematical quantities derived from the frequency domain data in one or more of the frequency bands. Each of the features (e.g., vector containing multiple features) may be further processed by the classifier, which can make a decision based on the functions. Some values of the features are correlated with fatigued while other values of the features are correlated with an absence of fatigued. Each of the features f1', f2', and f3' may include a single value or a set of values. For example, each of the features may be a vector of values corresponding to the feature. Alternatively, each of the features f1', f2', and f3' may be added to a vector that includes other values (e.g., corresponding to other EEG data). The classifier 1212 "learns" (by executing statistical analysis procedures) which values of the features are correlated with fatigued and which other values of the features are correlated with an absence of fatigue.

As discussed above, pre-processing can produce truncated time windows of various sizes. This could pose a technical challenge because the features may be derived from a different basis (i.e., different length of time) relative to one another, which could preclude meaningful comparisons of the features.

A solution to such a challenge is to normalize the feature by the length of its truncated time window to produce a normalized time window (value of feature divided by a length of the truncated time window). The normalized time window can be conceptualized as a sort of "unit" time window (where the length is effectively equal to one) or as an average value for the truncated time window. Thus, a feature of the normalized time window can be calculated for each of the truncated time windows, regardless of the variations in size. Such normalization enables meaningful comparisons of features of the normalized time window due to the features derived from a common basis (e.g., a unit length of time). Values of the features and/or the normalized features are input to the classifier 1212.

As an illustrative example, a feature may include an area under the curve of a function. The area may be calculated by integrating the function. In such an example, each of the features f1', f2', and f3' may be calculated by integrating the corresponding function (i.e., f1, f2, and f3, respectively). To account for variations in size of truncated time windows, the area (i.e., a specific numerical value of area) is normalized by the length of the truncated time window, which is 14 seconds in the example of FIG. 12.

Because the FFT can produce a corresponding frequency domain representation for each of the EEG data signals, the feature (e.g., in this case normalized area) are calculated for each of the corresponding representations. Thus, in this case, where there are four channels of EEG data (TP9, AF7, AF8, and TP9) from which to calculate each of three features (f1', f2', and f3'), a total of 12 features is calculated (i.e., 4 EEG data channels x 3 features). In other examples, where a different number of EEG data channels is used utilized, the total number of features is different (i.e., # of channels of EEG data X # of features). For example, if two channels of EEG data are utilized (e.g., AF7, AF8) from the example of FIG. 11B, then the total number of features is six (4 EEG data channels x 3 features). Such features may be added to a feature vector of length n (where in is the total number of features). The vector can be represented as a point in an n-dimensional hyperspace. The classifier 1212 can utilize these points as input to make a determination of whether a user is fatigued.

Figure 14:
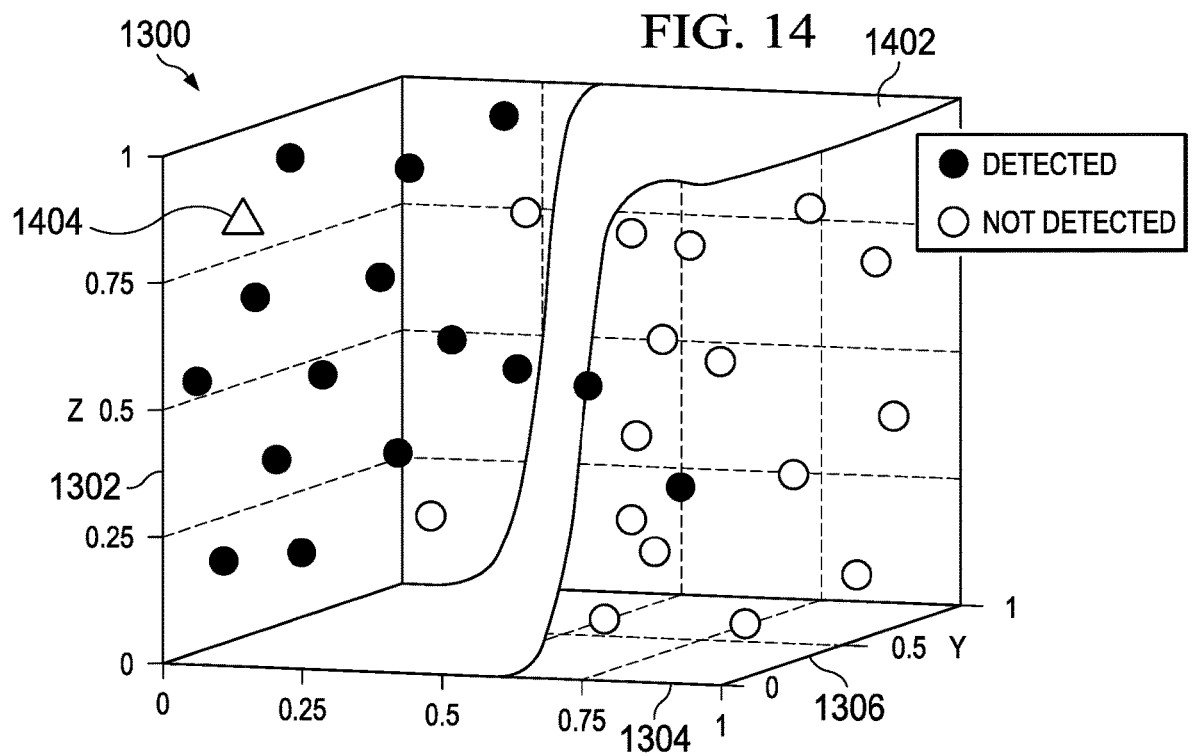

Turning to FIGS. 13 and 14, illustrate an example of training a classifier and subsequent decision making by the classifier after training. The Figures are graphical representation of input to and output from code (when executed) corresponding to the classifier.

FIG. 13 illustrates a graph 1300 of a portion of a three-dimensional space in which a set of points (i.e., labeled examples) are plotted. The graph 1300 includes an x-axis 1304, a y-axis 1306, and a z-axis 1302, each of which is perpendicular to others of the axes. Each point includes three values, each of which is values of a feature (spectral feature) for a time window of EEG data (e.g., calculated as described with respect to FIGS. 10A-10C and 11-12) and each point is associated with a label (e.g., a vigilance decrement "detected" label and a vigilance decrement "not detected" label). This three-dimensional example is simply to illustrate the manner in which the training may be performed. The classifier may utilize points that include any number of features (n) and therefore may utilize an n-dimensional space (where n is any whole number greater than or equal to 1).

The labeled examples correspond to known outcomes determined by performing an experiment on a set of individuals to collect EEG data. For example, the data may be collected by testing users over a period of time (e.g., an hour or longer). During the period of time, EEG data is collected from the users while the users are asked to respond to a stimulation (e.g., an appearance of a light on a screen) by clicking a button. The users respond by clicking a button. The stimulation is infrequent (e.g., about every 3 minutes) and irregular (e.g., by introducing a pseudo random delay to the timing of the stimulation). A first time is a time which the stimulation is output. A second time is a time at which the response is received from the user. The user user's vigilance is determined based on a comparison of the first time and the second time (difference). The user is determined to have lost focus (or become fatigued) in instances where the difference between the first time and the second time is above a threshold. The user is determined to have not lost focus (or is not fatigued) in instances where the difference between the first time and the second time is below the threshold. The known outcomes the results of such a test, the data from which is used to create the labeled examples.

The data plotted in FIG. 13 is used as input to train the classifier, which in this example a support vector machine (SVM) classifier. In particular, the data are examples that used to train the SVM classifier to distinguish when a user has lost focused (i.e., the "detected" label) versus when a user has not lost focus (i.e., the "not detected" label). To "learn" such a distinction, the SVM classifier executes a training routine on the data identify a function that distinguishes between the two labels. The training routine may include one or more mathematical operations and/or statistical analysis operations (e.g., regression). In one example, code corresponding to a training routine of the classifier comprises instructions to: receive features labeled, each of which is associated with one of two or more labels (e.g., the labeled examples plotted in FIG. 13), analyze the labeled features to determine a function (a function corresponding to a plane) that delineates a boundary between the two or more labels. The code may further include code to receive a kernel type (e.g., linear, quadratic, polynomial, sigmoid, radial basis function, and the like) and determine the function based on the kernel type. The function is determined such that its shape corresponds to the kernel type. In this example, such a training routine (when executed on the labeled examples plotted in FIG. 13, with a sigmoid kernel type), generates a plane 1402 of FIG. 14.

Turning to FIG. 14, illustrates the graph 1300 (of FIG. 13) at a point in which the classifier has generated the plane 1402 to delineate a boundary between the "detected" and "not detected" labels. The graph includes the data and axes as described with respect to FIG. 13; the details are not repeated here only for brevity. The classifier used the kernel type to determine the general shape of the plane used to distinguish between the points. The shape of the plane 1402 corresponds to a sigmoid function. In this example, a vast majority the points on the left side of the plane 1402 are of the "detected" label and a vast majority the points on the right side of the plane 1402 are of the "not detected" label. A few points on the left side are of the "not detected" label. Likewise, a few points on the right side are of the "detected" label. These few points mean that the function is not a "perfect" fit for the data (and therefore may be give perfect predictions of fatigue, the data outputs predictions that are correct a vast majority of the time.

In this example, because the classifier has already been trained, a new set of unlabeled inputs can be received for processing by the trained classifier (to determine a label).

A point 1404 is a new, unlabeled input received by the classifier. The classifier determines that the point 1404 lies on a side of the plane 1402 that corresponds to the "detected" label. Based on the determination, the classifier outputs data indicative of the determination that the user has lost focus. For example, the classifier may output the "detected" label, TRUE, or other data indicative of the determination. Such a determination may be used, e.g., to log data on a person's attentiveness over time or to activate a system. In one example, code corresponding to the classifier comprises instructions to: receive input features (e.g., the point 1404, which is unlabeled), determine which of two or more labels (e.g., the "detected" label, the "not detected" label) corresponds to the input features based on a sigmoid function that delineates a boundary between the two or more labels (e.g., the plane 1402), and output one of two or more labels based on the determination.

Figure 15:
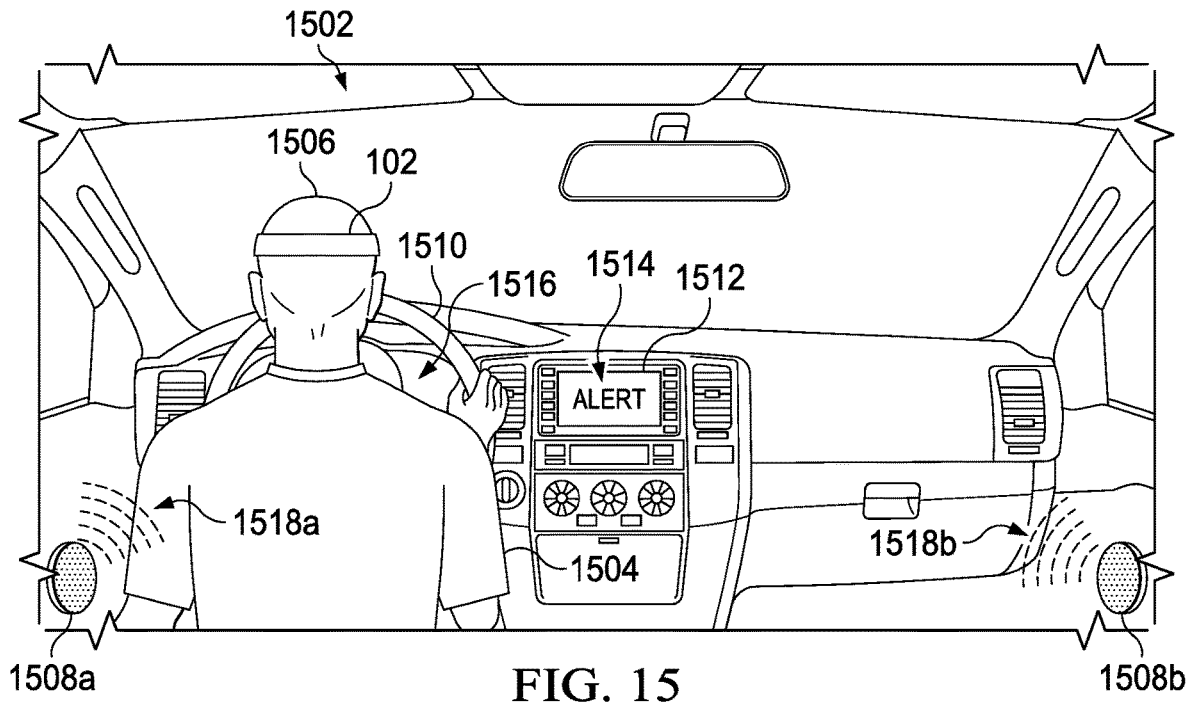
FIG. 15 illustrates a vehicle alerting an operator of the vehicle based on EEG data measured by a head-mountable device 102, according to some embodiments of the present disclosure.

Turning to FIG. 15, FIG. 15 illustrates a vehicle 1502 alerting an operator 1504 of the vehicle 1502 based on data measured by a head-mountable device 102, according to some embodiments of the present disclosure. The vehicle 1502 comprises: a steering wheel 1510, a dashboard 1516, a display screen 1512, and speakers 1508*a* and 1508*b*. The display screen 1512 is a visual output system and is configured to display graphics. The graphics can include, e.g., images and/or text. In some examples, the graphics correspond to a message for the operator 1504 and/or passengers of the vehicle 1502. The speakers 1508*a* and 1508*b* comprise an audio output system and are configured to produce sound. In some examples, the sound corresponds to a message for the operator 1504 and/or passengers of the vehicle 1502. The head-mountable device 102 of FIG. 15 may include any combination of one or more features of the head-mountable devices disclosed herein (e.g., FIGS. 1, 2, 17A, 17B, 18, 19, and/or 20).

The head-mountable device 102 is attached to a head 1506 of the operator 1504 (i.e. the wearer of the head-mountable device 102). At least one EEG electrode on the head-mountable device 102 collects EEG data based on contact with the operator's 1504 head 1506. The operator 1504 controls operation of the vehicle 1502, at least in part, using the steering wheel 1510 and monitors the operation (e.g., speed) of the vehicle using the dashboard 1516. A wireless data connection operably couples the head-mountable device 102 and the vehicle 1502 to one another and provides a conduit over which to transmit and/or receive data. As an example, they may be coupled through the Internet or by a direct BLUETOOTH connection.

As the operator 1504 controls the vehicle 1502, the head-mountable device 102 collects EEG data on the operator 1504. The EEG data or, e.g., features derived from spectral analysis of the EEG data are used to determine whether the operator 1504 is fatigued. Such a determination can be made by either the head-mountable device 102, or the vehicle 1502, or a remote device (e.g., a server). In some examples, the head-mountable device 102 transmits the EEG data or a representation of the EEG data to remote device, which processes the data to makes the determination and, ultimately, transmit an indication of the determination to the vehicle 1502. In other examples, the head-mountable device 102 can transmit an indication of the determination to the vehicle 1502 (e.g., upon making the termination itself). Alternatively, the vehicle 1502 may be equipped with a processor to process the EEG data or representations thereof to make directly the determination.

Regardless of which device (i.e., the head-mountable device 102, the remote device, or the vehicle 1502) makes the determination of whether the operator 1504 is fatigued, data indicative of the determination is received by the vehicle 1502.

The vehicle 1502 can activate output systems based on data indicating that the operator 1504 is fatigued (e.g., a vigilance decrement state). In the example, of FIG. 15, a processor onboard the vehicle 1502 is: (1) activating the speakers 1508a and 1508b to produce sounds 1518a and 1518b respectively, (2) activating the display screen 1512 to display a text alert 1514 (i.e., "ALERT!"), and (3) activating a vibratory alert system within the steering wheel 1510 (e.g., intermittent pulses of vibrations at a frequency of about 180 Hz), based on receiving data indicating that the operator 1504 is fatigued. Each of the activations, e.g., disrupts a vigilant decrement state of the operator's 1504 brain and can help stimulate the operator's focus so that they can bring their full attention back to the task of operating the vehicle 1502.

Figure 16:
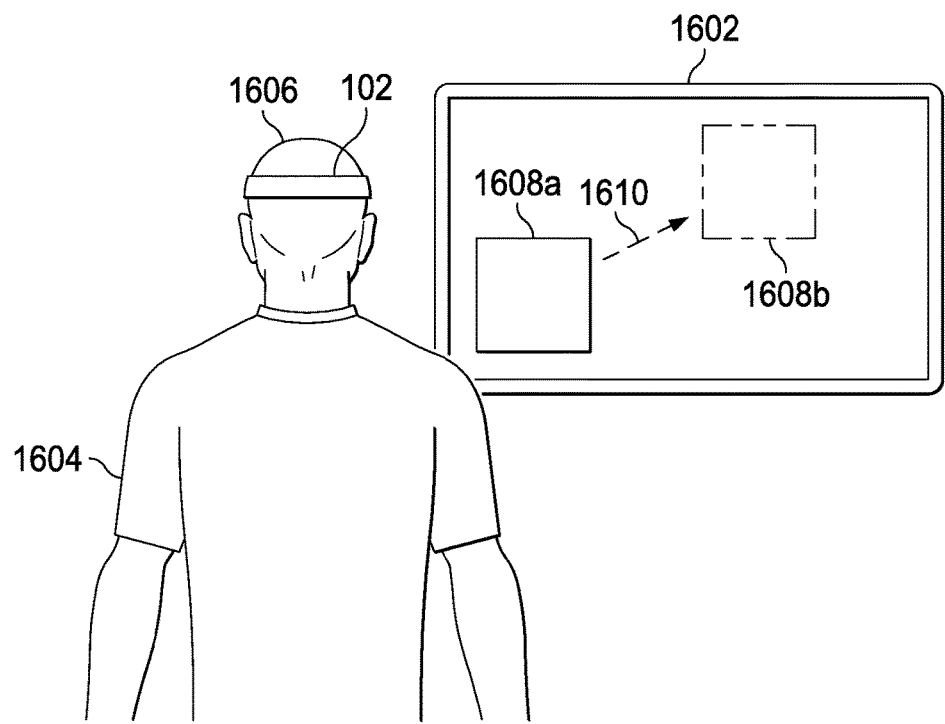
FIG. 16 illustrates a graphical interface actively modifying a location of a graphical component based on EEG data measured by a head-mountable device, according to some embodiments of the present disclosure.

Turning to FIG. 16, FIG. 16 illustrates a graphical interface 1602 actively modifying a location of a graphical component 1608 based on data measured by a head-mountable device 102, according to some embodiments of the present disclosure. The head-mountable device 102 of FIG. 16 may include any combination of one or more features of the head-mountable devices disclosed herein (e.g., FIGS. 1, 2, 17A, 17B, 18, 19, and/or 20). The graphical interface 1602 may be an interface corresponding to a productivity application (e.g. word processing interface, presentation software interface, virtual meeting), a gaming system, an augmented reality interface, or other interface. The head-mountable device 102 is attached to a head 1606 of the operator 1604 (i.e. the wearer of the head-mountable device 102). At least one EEG electrode on the head-mountable device 102 collects EEG data based on contact with the operator's head 1606. The graphical interface 1602 moves (i.e. as generally indicated by 1610) the graphical component 1608 from a first location (as generally indicated by 1608a) to a second location (as generally indicated by 1608b) based on a data (received from the head-mountable device 102) indicating that the operator 1504 is fatigued. Moving the graphical component 1608 forces the user to move their eye position (e.g., to rouse the user). The graphical interface 1602 applications adapt to the user's metal state. For example, the graphical interface 1602 move parts of app to a center of the user's focal point.

Figure 17A:
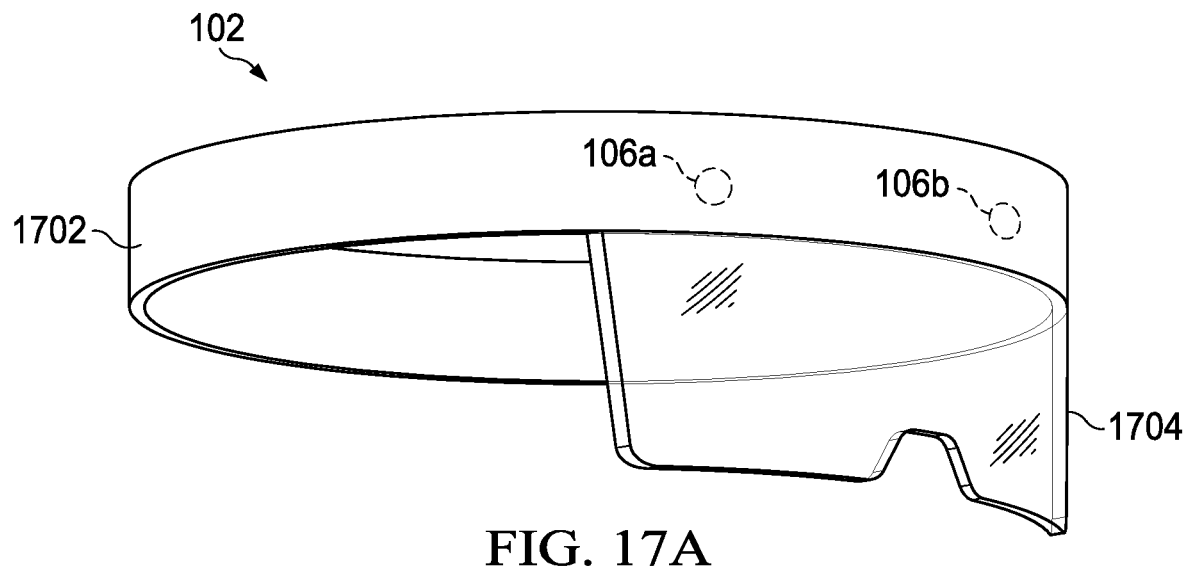
FIG. 17A illustrates a head-mountable device, according to some embodiments of the present disclosure.

Turning to FIG. 17A, FIG. 17A illustrates a head-mountable device 102, which in this example, is a network connectable pair of glasses (spectacles). The head-mountable device 102 comprises an attachment band 1702, electrodes 106a and 106b, and a heads-up display 1704. The attachment band 1702 is an attachment mechanism to attach the head-mountable device 102 to a wearer's head. The electrodes 106a and 106b, which are embedded in the attachment band 1702, are to collect EEG data based, in part, on contact with a wearer's head. The heads-up display 1704 extends from the attachment band 1702. The electrodes 106a and 106b and the heads-up display 1704 are operably coupled to one another. The head-mountable device 102 is configured to determine (based on EEG data from the electrodes) whether the wearer of the head-mountable device 102 is fatigued.

Figure 17B:
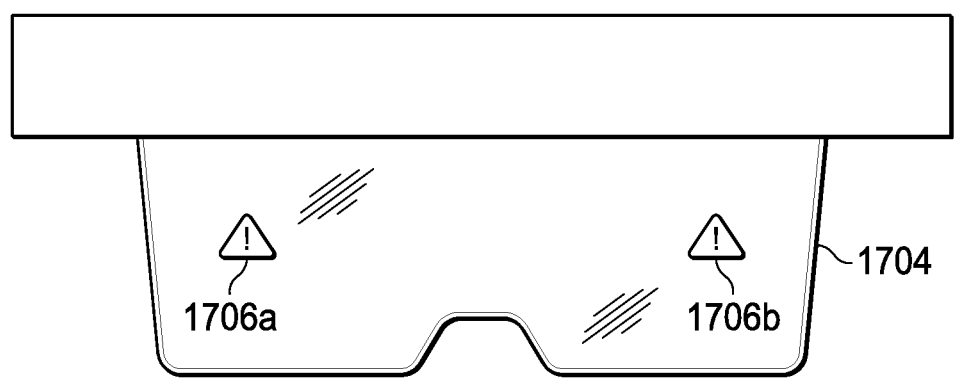
FIG. 17B illustrates a view through a display on the head-mountable device of FIG. 17A.

Turning to FIG. 17B, FIG. 17B illustrates a view through the heads-up display 1704 on the head-mountable device 102 of FIG. 17A. In this example, the heads-up display 1704 displays alert icons 1706a and 1706b based on processing EEG data collected from the electrodes 106a and 106b and determining (based on the processing) that the wearer of the head-mountable device 102 is fatigued.

Figure 18:
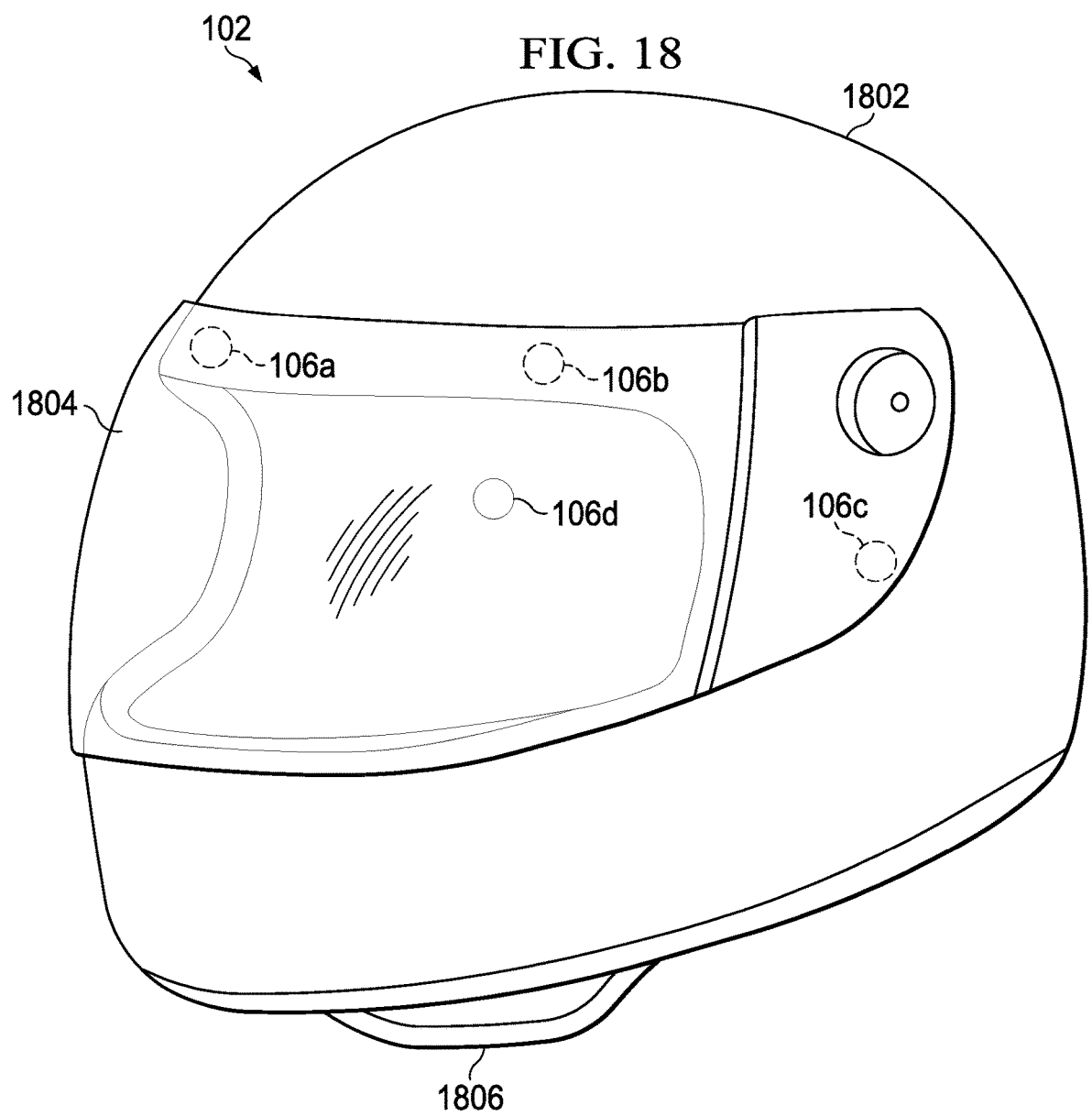
FIGS. 18, 19, and 20 illustrate head-mountable devices, according to some embodiments of the present disclosure.

Turning to FIG. 18, FIG. 18 illustrates a head-mountable device 102, which in this example, is a protective helmet. As an example, the protective helmet may be used for operators of a velocipede, a motorcycle, or other vehicle where the operator is substantially exposed to bodily harm (i.e., and not inherently protected by the vehicle itself).

The head-mountable device 102 comprises a housing 1802, a shield 1804, an attachment mechanism 1806, and electrodes 106a, 106b, 106c, and 106d. The head-mountable device 102 may communicate with the user's vehicle itself, or may communicate with a mobile device associated with the user. For example, the head-mountable device 102 can transmit a message to a motorcycle and/or the mobile device indicating that the wearer of the helmet is fatigued. The mobile phone may vibrate in the user's pocket to rouse their attention. Advantageously, a user wearing the head-mountable device 102 with the EEG electrodes embedded therein may be less likely to lose focus and/or to succumb to fatigue and, consequently, lose control of the vehicle. Because the head-mountable device 102 proactively detects brain activity indicative of fatigue, the user may be alerted before they succumb to the fatigue.

Figure 19:
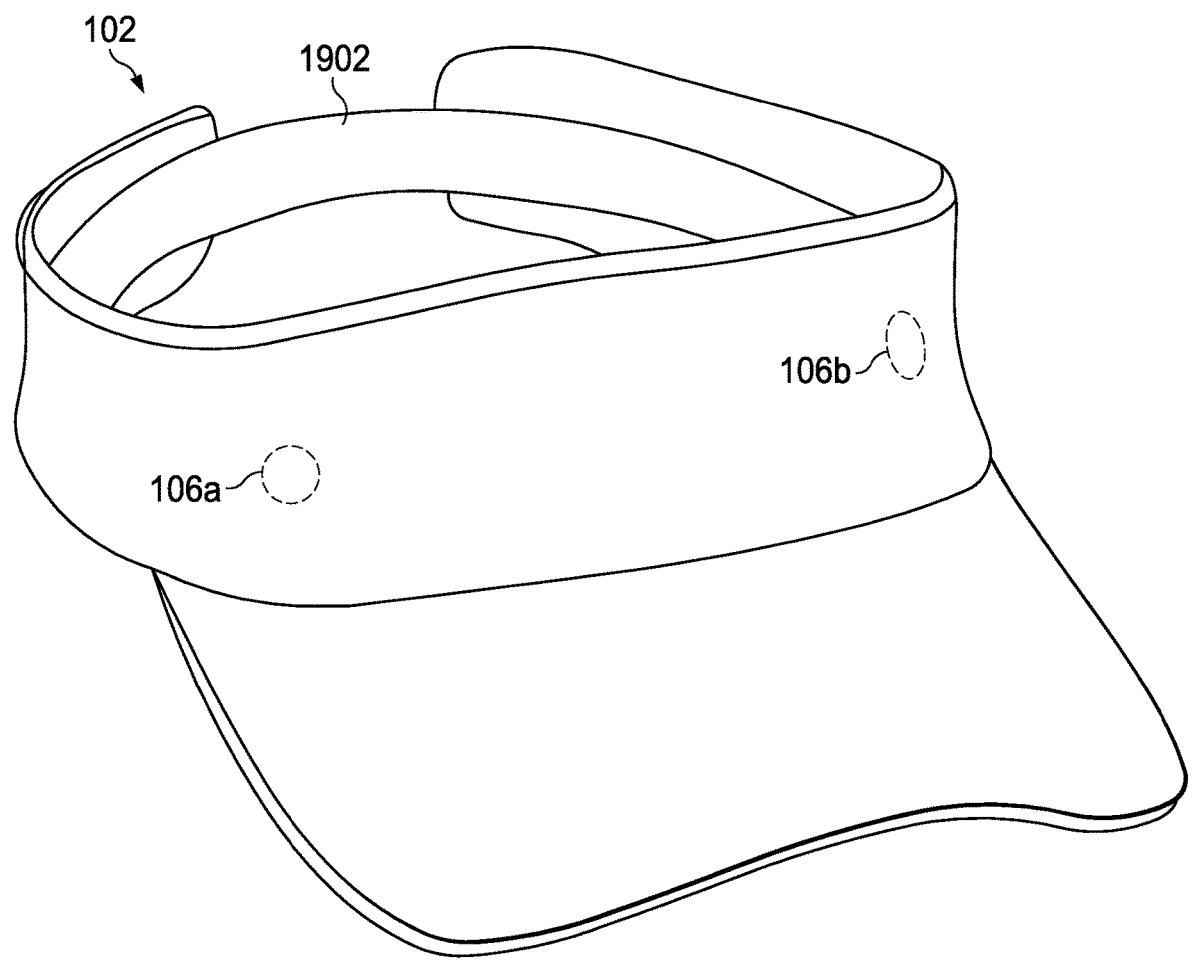

Turning to FIG. 19, FIG. 19 illustrates a head-mountable device 102, which in this example, is a visor. The head-mountable device 102 comprises electrodes 106a and 106b and an attachment band 1902 embedded in the body of the head-mountable device 102. The head-mountable device 102 is configured to determine (based on EEG data from the electrodes 106a and 106b) whether the wearer of the head-mountable device 102 is fatigued. Such a head-mountable device is particularly useful in situations where a user wants to wear the head-mounted device in a manner that does not disrupt their normal work activities. For example, a professional driver (e.g., in public transportation, chauffeur, and the like) may benefit from such the head-mounted device, e.g., because it does not require gel to be effective and the visor form factor would look natural in their work environment (e.g., in contrast to unsightly full-scalp EEG caps).

Figure 20:
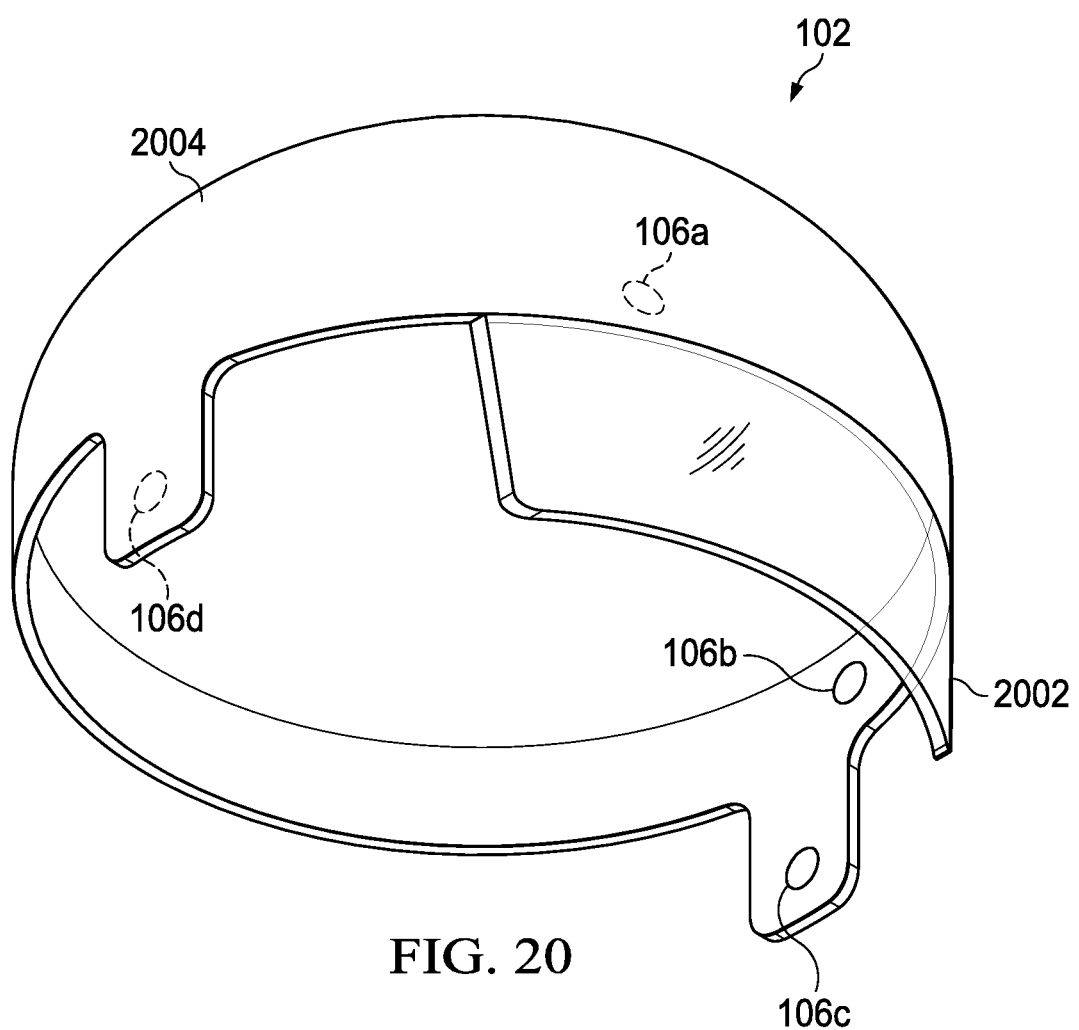

Turning to FIG. 20, FIG. 20 illustrates a head-mountable device 102, which in this example, is a helmet comprising a heads-up display. The head-mountable device 102 comprises a housing 2004, electrodes 106a, 106b, 106c, and 106d, and a heads-up display 2002. The head-mountable device 102 is configured to determine (based on EEG data from the dry-contact EEG electrodes 106a, 106b, 106c, and 106d) whether the wearer of the head-mountable device 102 is fatigued. The heads-up display 2002 can display graphical data (e.g., messages, alerts, text, images, and the like) based on determining that the wearer of the head-mountable device 102 is fatigued.

The following examples pertain to further embodiments disclosed herein.

Example 1 is a head-mountable device comprising: a dry-contact electroencephalogram (EEG) electrode configured to measure EEG data, the EEG data comprising prefrontal cortex EEG data corresponding to activity of a prefrontal cortex of a brain; and a processor operably coupled to the dry-contact EEG electrode, wherein the processor is configured to: calculate a frequency domain representation of the EEG data, wherein the frequency domain representation comprises frequency data for the EEG data in each of a plurality of frequency bands, the plurality of frequency bands comprising: a first band, a second band, a third band, and a fourth band; calculate spectral features indicative of fatigue based on the frequency domain representation, the spectral features comprising: a first combination of the frequency data in each of the fourth band, the third band, and the first band; a second combination of the frequency data in each of the first band and the second band; and a third combination of the frequency data in each of the second band, the first band, and the third band; and detect fatigue associated with the brain based on the spectral features.

Example 2 may include the subject matter of Example 1, and may further specify that the first band is centered at about 6 hertz, the second band is centered at about 12 hertz, the third band is centered at about 23 hertz, and fourth band is centered at about 40 hertz.

Example 3 may include the subject matter of any one of Examples 1-2, and may further specify that: the first band comprising frequencies $x1$, where 4 hertz$\leq x1 <$8 hertz, the second band comprising frequencies $x2$, where 8 hertz$\leq x2 <$16 hertz, the third band comprising frequencies $x3$, where 16 hertz$\leq x3 <$30 hertz, and the fourth band comprising frequencies $x4$, where 30 hertz$\leq x4 <$50 hertz.

Example 4 may include the subject matter of any one of Examples 1-3, may further specify that: the first combination comprises a first function of (the fourth band+the third band)/the first band, the second combination comprises a second function of the first band/the second band, and the third combination comprises a third function of (the second band+the first band)/the third band.

Example 5 may include the subject matter of any one of Examples 1-4, may further specify that the processor is configured to: access a code corresponding to a classifier, the code comprising instructions to: receive input features, determine which one of two or more labels corresponds to the input features based on a sigmoid function that delineates a boundary between the two or more labels, and output one of two or more labels based on the one of two or more labels; and execute the code, wherein the input features comprise the spectral features.

Example 6 may include the subject matter of any one of Examples 1-5, may further specify that the processor is configured to: disrupt the fatigue associated with the brain by outputting, via an output system coupled to the head-mountable device, a sensory stimulation based on the detection of the fatigue associated with the brain.

Example 7 may include the subject matter of any one of Examples 1-6, and may further specify that the dry-contact EEG electrode measures the EEG data in a time domain, and the EEG data comprises an amplitude that varies with respect to time.

Example 8 may include the subject matter of Example 7, and may further specify that the processor is configured to transform a time window of the EEG data from the time domain to the frequency domain representation in a frequency domain.

Example 9 may include the subject matter of Example 8, and may further specify that the processor is configured to: receive the EEG data from the dry-contact EEG electrode; and store, in a memory, the time window of the EEG data.

Example 10 may include the subject matter of Example 9, and may further specify that the processor is configured to: remove spurious data from the time window of the EEG data to produce a truncated time window of the EEG data.

Example 11 may include the subject matter of Example 10, and may further specify that the processor is configured to identify the spurious data within at least one sub-window of the time window based on the spurious data deviating from a noise floor of the dry-contact EEG electrode.

Example 12 may include the subject matter of Example 11, and may further specify that the spurious data comprises a muscle artifact.

Example 13 may include the subject matter of any one of Examples 1-12, and may further specify that the head-mountable device is configured to hold the dry-contact EEG electrode a location corresponding to the prefrontal cortex of the brain.

Example 14 may include the subject matter of Example 13, and may further specify that the location conforms to a standard for EEG placement.

Example 15 may include the subject matter of Example 14, and may further specify that the standard comprises a 10-10 system published by an International Federation of Clinical Neurophysiology and the location is selected from the group consisting of AF7 of the 10-10 system and AF8 of the 10-10 system.

Example 16 may include the subject matter of any one of Examples 1-15, and may further comprise the output system, the output system being onboard the head-mountable device.

Example 17 may include the subject matter of any one of Examples 1-16, and may further comprise a communication interface configured to couple the output system to the head-mountable device.

Example 18 may include the subject matter of Example 6 or 17, and may further specify that the output system is external to the head-mountable device.

Example 19 The may include the subject matter of any one of Examples 6 and 16-18, and may further specify that the sensory stimulation is selected from the group consisting of an audible sound, a visible light, and a vibration.

Example 20 may include the subject matter of any one of Examples 6 and 16-19, and may further specify that the output system is selected from the group consisting of an audio output system, a visual output system, and a tactile output system.

Example 21 may include the subject matter of any one of Examples 6 and 16-20, and may further specify that: the audio output system is configured to output the audible sound, the visual output system is configured to output the visible light, and the tactile output system is configured to output the vibration.

Example 22 may include the subject matter of any one of Examples 6 and 16-20, may further specify that the output system comprises an audiovisual system configured to output the audible sound and the visible light.

Example 23 may include the subject matter of any one of Examples 6 and 17-22, and may further comprise a wireless communication interface to couple the head-mountable device to a gaming system, may further specify that the gaming system is coupled to the audiovisual system.

Example 24 may include the subject matter of any one of Examples 6 and 17-23, may further specify that the output system is coupled to a vehicle.

Example 25 may include the subject matter of Example 24, may further specify that the vehicle is selected from the group consisting of a motor vehicle, a locomotive, a railroad car, an aircraft, a velocipede, and a motorcycle.

Example 26 may include the subject matter of any one of Examples 6 and 17-25, and may further specify that the sensory stimulation comprises component of a graphical user interface.

Example 27 may include the subject matter of any one of Examples 1-26, and may further specify that the head-mountable device is selected from the group consisting of a helmet, a head band, a visor, and eyeglasses.

Example 28 may include the subject matter of any one of Examples 1-27, and may further specify that the dry-contact EEG electrode is a first dry-contact EEG electrode; and may further comprise: a second dry-contact EEG electrode to measure temporal lobe EEG data corresponding to activity of a temporal lobe of the brain, the temporal lobe EEG data comprised in the EEG data.

Example 29 may include the subject matter of Example 28, and may further specify that the head-mountable device is configured to hold the second dry-contact EEG electrode at a location corresponding to the temporal lobe of the brain.

Example 30 may include the subject matter of Example 29, and may further specify that the location conforms to a standard for EEG placement.

Example 31 may include the subject matter of Example 30, and may further specify that the standard comprises a 10-10 system published by an International Federation of Clinical Neurophysiology and the location is selected from the group consisting of TP9 of the 10-10 system and TP10 of the 10-10 system.

Example 32 may include the subject matter of any one of Examples 1-31, and may further specify that the dry-contact EEG electrode has an impedance of at least 100 kiloohms.

Example 33 may include the subject matter of any one of Examples 1-32, and may further comprise an attachment mechanism to secure the head-mountable device to a head of a person.

Example 34 is a machine readable non-transitory storage medium having instructions stored thereon, wherein the instructions, when executed by at least one processor, causes the at least one processor to perform operations comprising: receiving electroencephalogram (EEG) data from a dry-contact EEG electrode, the EEG data comprising prefrontal cortex EEG data corresponding to activity of a prefrontal cortex of a brain; calculating a frequency domain representation of the EEG data, wherein the frequency domain representation comprises frequency data for the EEG data in each of a plurality of frequency bands, the plurality of frequency bands comprising: a first band, a second band, a third band, and a fourth band; calculating spectral features indicative of fatigue based on the frequency domain representation, the spectral features comprising: a first combination of the frequency data in each of the fourth band, the third band, and the first band; a second combination of the frequency data in each of the first band and the second band; and a third combination of the frequency data in each of the second band, the first band, and the third band; and detecting fatigue associated with the brain based on the spectral features.

Example 35 may include the subject matter of Example 34, and may further specify that the first band is centered at about 6 hertz, the second band is centered at about 12 hertz, the third band is centered at about 23 hertz, and fourth band is centered at about 40 hertz.

Example 36 may include the subject matter of any one of Examples 34-35, and may further specify that: the first band comprising frequencies $x_1$, where 4 hertz$\leq x_1 <$8 hertz, the second band comprising frequencies $x_2$, where 8 hertz$\leq x_2 <$16 hertz, the third band comprising frequencies $x_3$, where 16 hertz$\leq x_3 <$30 hertz, and the fourth band comprising frequencies $x_4$, where 30 hertz$\leq x_4 <$50 hertz.

Example 37 may include the subject matter of any one of Examples 34-36, and may further specify that: the first combination comprises a first function of (the fourth band+the third band)/the first band, the second combination comprises a second function of the first band/the second band, and the third combination comprises a third function of (the second band+the first band)/the third band.

Example 38 may include the subject matter of any one of Examples 34-37, and may further specify that the operations comprise: determining which of two or more labels corresponds to the spectral features based on a sigmoid function that delineates a boundary between the two or more labels.

Example 39 may include the subject matter of any one of Examples 34-38, and may further specify that the operations comprise: disrupting the fatigue associated with the brain by outputting, via an output system, a sensory stimulation based on the detection of the fatigue associated with the brain.

Example 40 may include the subject matter of any one of Examples 34-39, and may further specify that the EEG data is measured in a time domain, may further specify that the EEG data comprises an amplitude that varies with respect to time.

Example 41 may include the subject matter of any one of Examples 34-40, and may further specify that the operations comprise: transforming a time window of the EEG data from the time domain to the frequency domain representation in a frequency domain.

Example 42 may include the subject matter of any one of Examples 34-41, and may further specify that the operations comprise: receiving the EEG data from the dry-contact EEG electrode; and storing, in a memory, the time window of the EEG data.

Example 43 may include the subject matter of any one of Examples 34-42, and may further specify that the operations comprise: removing spurious data from the time window of the EEG data to produce a truncated time window of the EEG data.

Example 44 may include the subject matter of any one of Examples 34-43, and may further specify that the operations comprise: identifying the spurious data within at least one sub-window of the time window based on the spurious data deviating from a noise floor of the dry-contact EEG electrode.

Example 45 may include the subject matter of any one of Examples 34-44, and may further specify that the spurious data comprises a muscle artifact.

Example 46 may include the subject matter of any one of Examples 34-45, and may further specify that the prefrontal cortex EEG data is received while the dry-contact EEG electrode is in contact with a location on a head of a user corresponding to the prefrontal cortex of the brain.

Example 47 may include the subject matter of any one of Examples 34-46, and may further specify that the location conforms to a standard for EEG placement.

Example 48 may include the subject matter of any one of Examples 34-47, and may further specify that the standard comprises a 10-10 system published by an International Federation of Clinical Neurophysiology and the location is selected from the group consisting of AF7 of the 10-10 system and AF8 of the 10-10 system.

Example 49 may include the subject matter of any one of Examples 34-48, and may further specify that the operations comprise: outputting the sensory stimulation via a head-mountable device, wherein the output system is onboard the head-mountable device.

Example 50 may include the subject matter of any one of Examples 34-49, and may further comprise: establishing a connection to the output system via a communication interface.

Example 51 may include the subject matter of Example 39 or 50, and may further specify that the EEG data is received from the dry-contact EEG electrode while the dry-contact EEG electrode is coupled to a head-mountable device; and may further specify that the output system is external to the head-mountable device.

Example 52 may include the subject matter of any one of Examples 39 and 49-51, and may further specify that the sensory stimulation is selected from the group consisting of an audible sound, a visible light, and a vibration.

Example 53 may include the subject matter of any one of Examples 39 and 49-52, and may further specify that the output system is selected from the group consisting of an audio output system, a visual output system, and a tactile output system.

Example 54 may include the subject matter of any one of Examples 39 and 49-53, and may further specify that the operations comprise: outputting the audible sound using the audio output system, outputting the visible light using the visual output system, and outputting the vibration using the tactile output system.

Example 55 may include the subject matter of any one of Examples 39 and 49-53, and may further specify that the output system comprises an audiovisual system and the operations comprise: outputting the audible sound and the visible light using the audiovisual system.

Example 56 may include the subject matter of any one of Examples 39 and 50-55, and may further comprise a wireless communication interface to couple the head-mountable device to a gaming system, may further specify that the gaming system is coupled to the audiovisual system.

Example 57 may include the subject matter of any one of Examples 39 and 50-56, and may further specify that the operations comprise: outputting the sensory stimulation via a vehicle, wherein the output system is coupled to the vehicle.

Example 58 may include the subject matter of Example 57, and may further specify that the vehicle is selected from the group consisting of a motor vehicle, a locomotive, a railroad car, an aircraft, a velocipede, and a motorcycle.

Example 59 may include the subject matter of any one of Examples 39 and 50-58, and may further specify that the sensory stimulation comprises component of a graphical user interface.

Example 60 may include the subject matter of any one of Examples 34-59, and may further specify that the machine readable non-transitory storage medium is in a head-mountable device selected from the group consisting of a helmet, a head band, a visor, and eyeglasses.

Example 61 may include the subject matter of any one of Examples 34-60, and may further specify that the dry-contact EEG electrode is a first dry-contact EEG electrode; and may further specify that the operations comprise: receiving temporal lobe EEG data from a second dry-contact EEG, the temporal lobe EEG data corresponding to activity of a temporal lobe of the brain, and wherein the temporal lobe EEG data is comprised in the EEG data.

Example 62 may include the subject matter of Example 61, and may further specify that the temporal lobe EEG data is received while the second dry-contact EEG electrode is in contact with a location on a head of a user corresponding to the temporal lobe of the brain.

Example 63 may include the subject matter of Example 62, and may further specify that the location conforms to a standard for EEG placement.

Example 64 may include the subject matter of Example 63, and may further specify that the standard comprises a 10-10 system published by an International Federation of Clinical Neurophysiology and the location is selected from the group consisting of TP9 of the 10-10 system and TP10 of the 10-10 system.

Example 65 may include the subject matter of any one of Examples 34-64, and may further specify that the dry-contact EEG electrode has an impedance of at least 100 kiloohms.

Example 66 is a method comprising: receiving electroencephalogram (EEG) data from a dry-contact EEG electrode, the EEG data comprising prefrontal cortex EEG data corresponding to activity of a prefrontal cortex of a brain; calculating a frequency domain representation of the EEG data, wherein the frequency domain representation comprises frequency data for the EEG data in each of a plurality of frequency bands, the plurality of frequency bands comprising: a first band, a second band, a third band, and a fourth band; calculating spectral features indicative of fatigue based on the frequency domain representation, the spectral features comprising: a first combination of the frequency data in each of the fourth band, the third band, and the first band; a second combination of the frequency data in each of the first band and the second band; and a third combination of the frequency data in each of the second band, the first band, and the third band; and detecting fatigue associated with the brain based on the spectral features.

Example 67 may include the subject matter of Example 66, wherein the first band is centered at about 6 hertz, the second band is centered at about 12 hertz, the third band is centered at about 23 hertz, and fourth band is centered at about 40 hertz.

Example 68 may include the subject matter of any one of Examples 66-67, and may further specify that: the first band comprising frequencies x1, where 4 hertz≤x1<8 hertz, the second band comprising frequencies x2, where 8 hertz≤x2<16 hertz, the third band comprising frequencies x3, where 16 hertz≤x3<30 hertz, and the fourth band comprising frequencies x4, where 30 hertz≤x4<50 hertz.

Example 69 may include the subject matter of any one of Examples 66-68, and may further specify that: the first combination comprises a first function of (the fourth band+the third band)/the first band, the second combination comprises a second function of the first band/the second band, and the third combination comprises a third function of (the second band+the first band)/the third band.

70 may include the subject matter of any one of Examples 66-69, and may further comprise: determining which of two or more labels corresponds to the spectral features based on a sigmoid function that delineates a boundary between the two or more labels.

Example 71 may include the subject matter of any one of Examples 66-70, and may further comprise: disrupting the fatigue associated with the brain by outputting, via an output system, a sensory stimulation based on the detection of the fatigue associated with the brain.

Example 72 may include the subject matter of any one of Examples 66-71, and may further specify that the EEG data is measured in a time domain, wherein the EEG data comprises an amplitude that varies with respect to time.

Example 73 may include the subject matter of any one of Examples 66-72, and may further comprise: transforming a time window of the EEG data from the time domain to the frequency domain representation in a frequency domain.

Example 74 may include the subject matter of any one of Examples 66-73, and may further comprise: receiving the EEG data from the dry-contact EEG electrode; and storing, in a memory, the time window of the EEG data.

Example 75 may include the subject matter of any one of Examples 66-74, and may further comprise: removing spurious data from the time window of the EEG data to produce a truncated time window of the EEG data.

Example 76 may include the subject matter of any one of Examples 66-75, and may further comprise: identifying the spurious data within at least one sub-window of the time window based on the spurious data deviating from a noise floor of the dry-contact EEG electrode.

Example 77 may include the subject matter of any one of Examples 66-76, and may further specify that the spurious data comprises a muscle artifact.

Example 78 may include the subject matter of any one of Examples 66-77, and may further specify that the prefrontal cortex EEG data is received while the dry-contact EEG electrode is in contact with a location on a head of a user corresponding to the prefrontal cortex of the brain.

Example 79 may include the subject matter of any one of Examples 66-78, and may further specify that the location conforms to a standard for EEG placement.

Example 80 may include the subject matter of any one of Examples 66-79, and may further specify that the standard comprises a 10-10 system published by an International Federation of Clinical Neurophysiology and the location is selected from the group consisting of AF7 of the 10-10 system and AF8 of the 10-10 system.

Example 81 may include the subject matter of any one of Examples 66-80, and may further comprise: outputting the sensory stimulation via a head-mountable device, wherein the output system is onboard the head-mountable device.

Example 82 may include the subject matter of any one of Examples 66-81, and may further comprise: establishing a connection to the output system via a communication interface.

Example 83 may include the subject matter of Example 71 or 82, and may further specify that the EEG data is received from the dry-contact EEG electrode while the dry-contact EEG electrode is coupled to a head-mountable device; and wherein the output system is external to the head-mountable device.

Example 84 may include the subject matter of any one of Examples 71 and 81-83, and may further specify that the sensory stimulation is selected from the group consisting of an audible sound, a visible light, and a vibration.

Example 85 may include the subject matter of any one of Examples 71 and 81-84, and may further specify that the output system is selected from the group consisting of an audio output system, a visual output system, and a tactile output system.

Example 86 may include the subject matter of any one of Examples 71 and 81-85, and may further comprise: outputting the audible sound using the audio output system, outputting the visible light using the visual output system, and outputting the vibration using the tactile output system.

Example 87 may include the subject matter of any one of Examples 71 and 81-85, and may further specify that the output system comprises an audiovisual system; and further comprising: outputting the audible sound and the visible light using the audiovisual system.

Example 88 may include the subject matter of any one of Examples 71 and 82-87, and may further comprise a wireless communication interface to couple the head-mountable device to a gaming system, wherein the gaming system is coupled to the audiovisual system.

Example 89 may include the subject matter of any one of Examples 71 and 82-88, and may further comprise: outputting the sensory stimulation via a vehicle, wherein the output system is coupled to the vehicle.

Example 90 may include the subject matter of Example 89, and may further specify that the vehicle is selected from the group consisting of a motor vehicle, a locomotive, a railroad car, an aircraft, a velocipede, and a motorcycle.

Example 91 may include the subject matter of any one of Examples 71 and 82-90, and may further specify that the sensory stimulation comprises component of a graphical user interface.

Example 92 may include the subject matter of any one of Examples 66-91, and may further specify that the EEG data is received from the dry-contact EEG electrode is in a head-mountable device selected from the group consisting of a helmet, a head band, a visor, and eyeglasses.

Example 93 may include the subject matter of any one of Examples 66-92, and may further specify that the dry-contact EEG electrode is a first dry-contact EEG electrode; and may further comprise: receiving temporal lobe EEG data from a second dry-contact EEG, the temporal lobe EEG data corresponding to activity of a temporal lobe of the brain, and wherein the temporal lobe EEG data is comprised in the EEG data.

Example 94 may include the subject matter of Example 93, and may further specify that the temporal lobe EEG data is received while the second dry-contact EEG electrode is in contact with a location on a head of a user corresponding to the temporal lobe of the brain.

Example 95 may include the subject matter of Example 94, and may further specify that the location conforms to a standard for EEG placement.

Example 96 may include the subject matter of Example 95, and may further specify that the standard comprises a 10-10 system published by an International Federation of Clinical Neurophysiology and the location is selected from the group consisting of TP9 of the 10-10 system and TP10 of the 10-10 system.

Example 97 may include the subject matter of any one of Examples 66-96, and may further specify that the dry-contact EEG electrode has an impedance of at least 100 kiloohms.

Example 98 is an apparatus comprising means to perform a method as specified in any of Examples 66-97.

Example 99 is a machine-readable storage including machine-readable instructions, when executed, to implement a method or realize an apparatus as specified in any of Examples 66-97.

Example 100 is a machine readable medium including code, when executed, to cause a machine to perform the methods of any one of Examples 66-97.

Example 101 is an apparatus comprising: a processor; and a memory coupled to the processor to store instructions, the instructions, when executed by the processor, to perform the methods of any one of Examples 66-97.

Example 102 is an apparatus comprising: means for receiving electroencephalogram (EEG) data from a dry-contact EEG electrode, the EEG data comprising prefrontal cortex EEG data corresponding to activity of a prefrontal cortex of a brain; means for calculating a frequency domain representation of the EEG data, wherein the frequency domain representation comprises frequency data for the EEG data in each of a plurality of frequency bands, the plurality of frequency bands comprising: a first band, a second band, a third band, and a fourth band; means for calculating spectral features indicative of fatigue based on the frequency domain representation, the spectral features comprising: a first combination of the frequency data in each of the fourth band, the third band, and the first band; a second combination of the frequency data in each of the first band and the second band; and a third combination of the frequency data in each of the second band, the first band, and the third band; and means for detecting fatigue associated with the brain based on the spectral features.

Example 103 may include the subject matter of Example 102, and may further specify that the first band is centered at about 6 hertz, the second band is centered at about 12 hertz, the third band is centered at about 23 hertz, and fourth band is centered at about 40 hertz.

Example 104 may include the subject matter of any one of Examples 102-103, and may further specify that: the first band comprising frequencies $x1$, where 4 hertz$\leq x1 <$8 hertz, the second band comprising frequencies $x2$, where 8 hertz$\leq x2 <$16 hertz, the third band comprising frequencies $x3$, where 16 hertz$\leq x3 <$30 hertz, and the fourth band comprising frequencies $x4$, where 30 hertz$\leq x4 <$50 hertz.

Example 105 may include the subject matter of any one of Examples 102-104, and may further specify that: the first combination comprises a first function of (the fourth band+ the third band)/the first band, the second combination comprises a second function of the first band/the second band, and the third combination comprises a third function of (the second band+the first band)/the third band.

Example 106 may include the subject matter of any one of Examples 102-105, and may further comprise: means for determining which of two or more labels corresponds to the spectral features based on a sigmoid function that delineates a boundary between the two or more labels.

Example 107 may include the subject matter of any one of Examples 102-106, and may further comprise: means for disrupting the fatigue associated with the brain by outputting a sensory stimulation based on the detection of the fatigue associated with the brain.

Example 108 may include the subject matter of any one of Examples 102-107, and may further specify that the EEG data is measured in a time domain, wherein the EEG data comprises an amplitude that varies with respect to time.

Example 109 may include the subject matter of any one of Examples 102-108, and may further comprise: means for transforming a time window of the EEG data from the time domain to the frequency domain representation in a frequency domain.

Example 110 may include the subject matter of Example 109, and may further comprise: means for receiving the EEG data from the dry-contact EEG electrode; and means for storing the time window of the EEG data.

Example 111 may include the subject matter of Example 110, and may further comprise: means for removing spurious data from the time window of the EEG data to produce a truncated time window of the EEG data.

Example 112 may include the subject matter of Example 111, and may further comprise: means for identifying the spurious data within at least one sub-window of the time window based on the spurious data deviating from a noise floor of the dry-contact EEG electrode.

Example 113 may include the subject matter of Example 112, and may further specify that the spurious data comprises a muscle artifact.

Example 114 may include the subject matter of any one of Examples 102-113, and may further specify that the prefrontal cortex EEG data is received while the dry-contact EEG electrode is in contact with a location on a head of a user corresponding to the prefrontal cortex of the brain.

Example 115 may include the subject matter of any one of Examples 102-114, and may further specify that the location conforms to a standard for EEG placement.

Example 116 may include the subject matter of any one of Examples 102-115, and may further specify that the standard comprises a 10-10 system published by an International Federation of Clinical Neurophysiology and the location is selected from the group consisting of AF7 of the 10-10 system and AF8 of the 10-10 system.

Example 117 may include the subject matter of Example 107, and may further comprise: means for outputting the sensory stimulation via a head-mountable device.

Example 118 may include the subject matter of any one of Examples 102-117, and may further comprise: means for establishing a connection to an output system.

Example 119 may include the subject matter of any one of Examples 102-117, and may further specify that the EEG data is received from the dry-contact EEG electrode while the dry-contact EEG electrode is coupled to a head-mountable device.

Example 120 may include the subject matter of any one of Examples 107 and 117-119, and may further specify that the sensory stimulation is selected from the group consisting of an audible sound, a visible light, and a vibration.

Example 121 may include the subject matter of any one of Examples 107 and 117-120, further comprising: means for outputting the audible sound, means for outputting the visible light, and means for outputting the vibration.

Example 122 may include the subject matter of any one of Examples 107 and 118-121, and may further comprise: means for outputting the sensory stimulation via a vehicle.

Example 123 may include the subject matter of Example 122, and may further specify that the vehicle is selected from the group consisting of a motor vehicle, a locomotive, a railroad car, an aircraft, a velocipede, and a motorcycle.

Example 124 may include the subject matter of any one of Examples 107 and 118-123, and may further specify that the sensory stimulation comprises component of a graphical user interface.

Example 125 may include the subject matter of any one of Examples 102-124, and may further specify that the EEG data is received from the dry-contact EEG electrode is in a head-mountable device selected from the group consisting of a helmet, a head band, a visor, and eyeglasses.

Example 126 may include the subject matter of any one of Examples 102-125, and may further specify that the dry-contact EEG electrode is a first dry-contact EEG electrode; and may further comprise: means for receiving temporal lobe EEG data from a second dry-contact EEG, the temporal lobe EEG data corresponding to activity of a temporal lobe of the brain, and wherein the temporal lobe EEG data is comprised in the EEG data.

Example 127 may include the subject matter of Example 126, and may further specify that the temporal lobe EEG data is received while the second dry-contact EEG electrode is in contact with a location on a head of a user corresponding to the temporal lobe of the brain.

Example 128 may include the subject matter of Example 127, and may further specify that the location conforms to a standard for EEG placement.

Example 129 may include the subject matter of Example 128, and may further specify that the standard comprises a 10-10 system published by an International Federation of Clinical Neurophysiology and the location is selected from the group consisting of TP9 of the 10-10 system and TP10 of the 10-10 system.

Example 130 may include the subject matter of any one of Examples 102-129, and may further specify that the dry-contact EEG electrode has an impedance of at least 100 kiloohms.

Example 131 may include the subject matter of any one of Examples 102-130, and may further specify that the apparatus is a computing device.

Example 132 may include the subject matter of any one of Examples 102-130, and may further specify that the apparatus is a vehicle.

Example 133 may include the subject matter of any one of Examples 102-130, and may further specify that the apparatus is a head-mountable device.

Example 134 is a system comprising: a head-mountable device comprising: a dry-contact electroencephalogram (EEG) electrode configured to measure EEG data corresponding to activity of a brain; and a processor operably coupled to the dry-contact EEG electrode, wherein the processor is configured to: calculate spectral features indicative of fatigue based on a frequency domain representation of the EEG data, and detect fatigue associated with the brain based on the spectral features; and a vehicle comprising an output system, wherein the output system of the vehicle is configured to generate a sensory stimulation based on the detection of the fatigue associated with the brain.

Example 135 may include the subject matter of Example 134, and may further specify that the vehicle is selected from the group consisting of a motor vehicle, a locomotive, a railroad car, an aircraft, a velocipede, and a motorcycle.

Example 136 may include the subject matter of any one of Examples 134-135, and may further specify that the head-mountable device is selected from the group consisting of a helmet, a head band, a visor, and eyeglasses.

Example 137 may include the subject matter of any one of Examples 134-136, and may further specify that the output system selected from a group consisting of: an audio output system, a visual output system, and/or a tactile output system.

Example 138 may include the subject matter of any one of Examples 134-136, and may further specify that a wearer of the head-mountable device is located in the vehicle.

Example 139 is a system comprising: a head-mountable device comprising: a dry-contact electroencephalogram (EEG) electrode configured to measure EEG data corresponding to activity of a brain; and a processor operably coupled to the dry-contact EEG electrode, wherein the processor is configured to: calculate spectral features indicative of fatigue based on a frequency domain representation of the EEG data, and detect fatigue associated with the brain based on the spectral features; and a mobile device comprising an output system, wherein the output system of the mobile device is configured to generate a sensory stimulation based on the detection of the fatigue associated with the brain.

Example 140 may include the subject matter of Example 139, and may further specify that the mobile device is selected from the group consisting of a cell phone, a tablet, a gaming console, and a computer.

Example 141 may include the subject matter of any one of Examples 139-140, and may further specify that the head-mountable device is selected from the group consisting of a helmet, a head band, a visor, and eyeglasses.

Example 142 may include the subject matter of any one of Examples 139-141, and may further specify that the output system selected from a group consisting of: an audio output system, a visual output system, and/or a tactile output system.

Example 143. A system comprising: a vehicle comprising an output system; a server coupled to the vehicle; a head-mountable device comprising: a dry-contact electroencephalogram (EEG) electrode configured to measure EEG data corresponding to activity of a brain; and a processor operably coupled to the dry-contact EEG electrode, wherein the processor is configured to transmit a representation of the EEG data to the server; wherein the server is configured to: calculate spectral features indicative of fatigue based on a frequency domain representation of the EEG data, and detect fatigue associated with the brain based on the spectral features; and wherein the output system of the vehicle is configured to generate a sensory stimulation based on the detection of the fatigue associated with the brain.

Example 144 may include the subject matter of Example 143, and may further specify that the vehicle is selected from the group consisting of a motor vehicle, a locomotive, a railroad car, an aircraft, a velocipede, and a motorcycle.

Example 145 may include the subject matter of any one of Examples 143-144, and may further specify that the head-mountable device is selected from the group consisting of a helmet, a head band, a visor, and eyeglasses.

Example 146 may include the subject matter of any one of Examples 143-145, and may further specify that the output system selected from a group consisting of: an audio output system, a visual output system, and/or a tactile output system.

Example 147 may include the subject matter of any one of Examples 143-146, and may further specify that a wearer of the head-mountable device is located in the vehicle.

Example 148 may include the subject matter of any one of Examples 143-147, and may further specify the server is configured to: receive the representation of the EEG data; and calculate the frequency domain representation of the EEG data based on the representation of the EEG data, wherein the frequency domain representation comprises frequency data for the EEG data in each of a plurality of frequency bands, the plurality of frequency bands comprising: a first band, a second band, a third band, and a fourth band, wherein the spectral features comprise: a first combination of the frequency data in each of the fourth band, the third band, and the first band; a second combination of the frequency data in each of the first band and the second band; and a third combination of the frequency data in each of the second band, the first band, and the third band.

What is claimed is:

1. A head-mountable device comprising:
   a dry-contact electroencephalogram (EEG) electrode configured to measure EEG data, the EEG data comprising prefrontal cortex EEG data corresponding to activity of a prefrontal cortex of a brain; and
   a processor operably coupled to the dry-contact EEG electrode, wherein the processor is configured to:
   calculate a frequency domain representation of the EEG data, wherein the frequency domain representation comprises frequency data for the EEG data in each of a plurality of frequency bands, the plurality of frequency bands comprising: a first band, a second band, a third band, and a fourth band;
   calculate spectral features indicative of fatigue based on the frequency domain representation, the spectral features comprising: a first mathematical combination of the frequency data in each of the fourth band, the third band, and the first band; a second mathematical combination of the frequency data in each of the first band and the second band; and a third mathematical combination of the frequency data in each of the second band, the first band, and the third band; and detect fatigue associated with the brain based on the spectral features utilizing the first, the second, and the third combinations.

2. The head-mountable device of claim 1, wherein the first band is centered at about 6 hertz, the second band is centered at about 12 hertz, the third band is centered at about 23 hertz, and the fourth band is centered at about 40 hertz.

3. The head-mountable device of claim 1, wherein:
the first mathematical combination comprises a first function of (the fourth band+the third band)/the first band,
the second mathematical combination comprises a second function of the first band/the second band, and
the third mathematical combination comprises a third function of (the second band+the first band)/the third band.

4. The head-mountable device of claim 1, wherein the processor is configured to:
disrupt the fatigue associated with the brain by outputting, via an output system coupled to the head-mountable device, a sensory stimulation based on the detection of the fatigue associated with the brain.

5. The head-mountable device of claim 4, wherein the sensory stimulation is selected from a group consisting of an audible sound, a visible light, and a vibration.

6. The head-mountable device of claim 4, wherein the output system is selected from a group consisting of an audio output system, a visual output system, and a tactile output system.

7. The head-mountable device of claim 4, wherein the output system is coupled to a vehicle.

8. The head-mountable device of claim 1, wherein the processor is configured to transform a time window of the EEG data from a time domain to the frequency domain representation in a frequency domain.

9. The head-mountable device of claim 8, wherein the processor is further configured to:
remove spurious data from the time window of the EEG data to produce a truncated time window of the EEG data.

10. A machine readable non-transitory storage medium having instructions stored thereon, wherein the instructions, when executed by at least one processor, causes the at least one processor to perform operations comprising:
receiving electroencephalogram (EEG) data from a dry-contact EEG electrode, the EEG data comprising prefrontal cortex EEG data corresponding to activity of a prefrontal cortex of a brain;
calculating a frequency domain representation of the EEG data, wherein the frequency domain representation comprises frequency data for the EEG data in each of a plurality of frequency bands, the plurality of frequency bands comprising: a first band, a second band, a third band, and a fourth band;
calculating spectral features indicative of fatigue based on the frequency domain representation, the spectral features comprising: a first mathematical combination of the frequency data in each of the fourth band, the third band, and the first band; a second mathematical combination of the frequency data in each of the first band and the second band; and a third mathematical combination of the frequency data in each of the second band, the first band, and the third band; and
detecting fatigue associated with the brain based on the spectral features utilizing the first, the second, and the third combinations.

11. The machine readable non-transitory storage medium of claim 10, wherein the first band is centered at about 6 hertz, the second band is centered at about 12 hertz, the third band is centered at about 23 hertz, and the fourth band is centered at about 40 hertz.

12. The machine readable non-transitory storage medium of claim 10, wherein the operations further comprise:
determining which of two or more labels corresponds to the spectral features based on a sigmoid function that delineates a boundary between the two or more labels.

13. The machine readable non-transitory storage medium of claim 10, wherein the operations further comprise:
disrupting the fatigue associated with the brain by outputting, via an output system, a sensory stimulation based on the detection of the fatigue associated with the brain.

14. The machine readable non-transitory storage medium of claim 13, wherein the sensory stimulation is selected from a group consisting of an audible sound, a visible light, and a vibration.

15. The machine readable non-transitory storage medium of claim 13, wherein the output system is selected from a group consisting of an audio output system, a visual output system, and a tactile output system.

16. The machine readable non-transitory storage medium of claim 10, wherein the operations further comprise:
transforming a time window of the EEG data from a time domain to the frequency domain representation in a frequency domain.

17. The machine readable non-transitory storage medium of claim 16, wherein the operations further comprise:
removing spurious data from the time window of the EEG data to produce a truncated time window of the EEG data.

18. A method comprising:
receiving electroencephalogram (EEG) data from a dry-contact EEG electrode, the EEG data comprising prefrontal cortex EEG data corresponding to activity of a prefrontal cortex of a brain;
calculating a frequency domain representation of the EEG data, wherein the frequency domain representation comprises frequency data for the EEG data in each of a plurality of frequency bands, the plurality of frequency bands comprising: a first band, a second band, a third band, and a fourth band;
calculating spectral features indicative of fatigue based on the frequency domain representation, the spectral features comprising: a first mathematical combination of the frequency data in each of the fourth band, the third band, and the first band; a second mathematical combination of the frequency data in each of the first band and the second band; and a third mathematical combination of the frequency data in each of the second band, the first band, and the third band; and
detecting fatigue associated with the brain based on the spectral features utilizing the first, the second, and the third combinations.

19. The method of claim 18, wherein the first band is centered at about 6 hertz, the second band is centered at about 12 hertz, the third band is centered at about 23 hertz, and the fourth band is centered at about 40 hertz.

20. The method of claim 18, further comprising:
    determining which of two or more labels corresponds to the spectral features based on a sigmoid function that delineates a boundary between the two or more labels.

21. The method of claim 18, further comprising:
    disrupting the fatigue associated with the brain by outputting, via an output system, a sensory stimulation based on the detection of the fatigue associated with the brain.

22. The method of claim 21, wherein the sensory stimulation is selected from a group consisting of an audible sound, a visible light, and a vibration.

23. The method of claim 18, further comprising:
    transforming a time window of the EEG data from a time domain to the frequency domain representation in a frequency domain.

24. The method of claim 23, further comprising:
    removing spurious data from the time window of the EEG data to produce a truncated time window of the EEG data.

\* \* \* \* \*